United States Patent [19]

Hori et al.

[11] Patent Number: 5,662,584

[45] Date of Patent: Sep. 2, 1997

[54] ENDOSCOPE WITH POSITION DISPLAY FOR ZOOM LENS UNIT AND IMAGING DEVICE

[75] Inventors: Koichiro Hori; Herbert A. Thaler, both of Framingham, Mass.

[73] Assignee: Vista Medical Technologies, Inc., Carlsbad, Calif.

[21] Appl. No.: 545,927

[22] Filed: Oct. 20, 1995

Related U.S. Application Data

[63] Continuation-in-part of Ser. No. 319,886, Oct. 7, 1994, Pat. No. 5,582,576.

[51] Int. Cl.$^6$ .............................. A61B 1/045; A61B 1/05
[52] U.S. Cl. ..................... 600/103; 600/118; 600/167; 600/168; 348/65
[58] Field of Search ..................... 600/103, 109, 600/117, 118, 160, 167, 168, 173; 348/65, 71, 76

[56] References Cited

U.S. PATENT DOCUMENTS

| | | | |
|---|---|---|---|
| 3,817,635 | 6/1974 | Kawahara | 600/117 |
| 4,277,168 | 7/1981 | Oku | 600/117 |
| 4,488,039 | 12/1984 | Sato et al. | 600/109 |
| 4,846,155 | 7/1989 | Kimura | 600/167 |
| 5,503,320 | 4/1996 | Webster et al. | 600/117 |
| 5,506,912 | 4/1996 | Nagasaki et al. | 600/103 |

*Primary Examiner*—RIchard J. Apley
*Assistant Examiner*—John P. Leubecker
*Attorney, Agent, or Firm*—Pandiscio & Pandiscio

[57] ABSTRACT

A position-indicating video display system is provided for an endoscope of the type having an objective lens, a movable zoom lens, a movable solid state imaging device for picking up the image formed by said objective lens and transferred by said zoom lens, means for generating a visual display of the image seen by the objective lens, and control means for moving the zoom lens and the imaging device so as to assure that for each position occupied by the zoom lens the imaging device is positioned so that the its image-receiving surface is in the focal plane of the zoom lens. The position-indicating video display system comprises means for generating first and second movable markers indicative of the instantaneous positions of the zoom lens and the solid state imaging device along the optical axis, and additional limit markers indicative of the maximum and minimum limits of the travel paths of the zoom lens and the solid state imaging device.

14 Claims, 27 Drawing Sheets

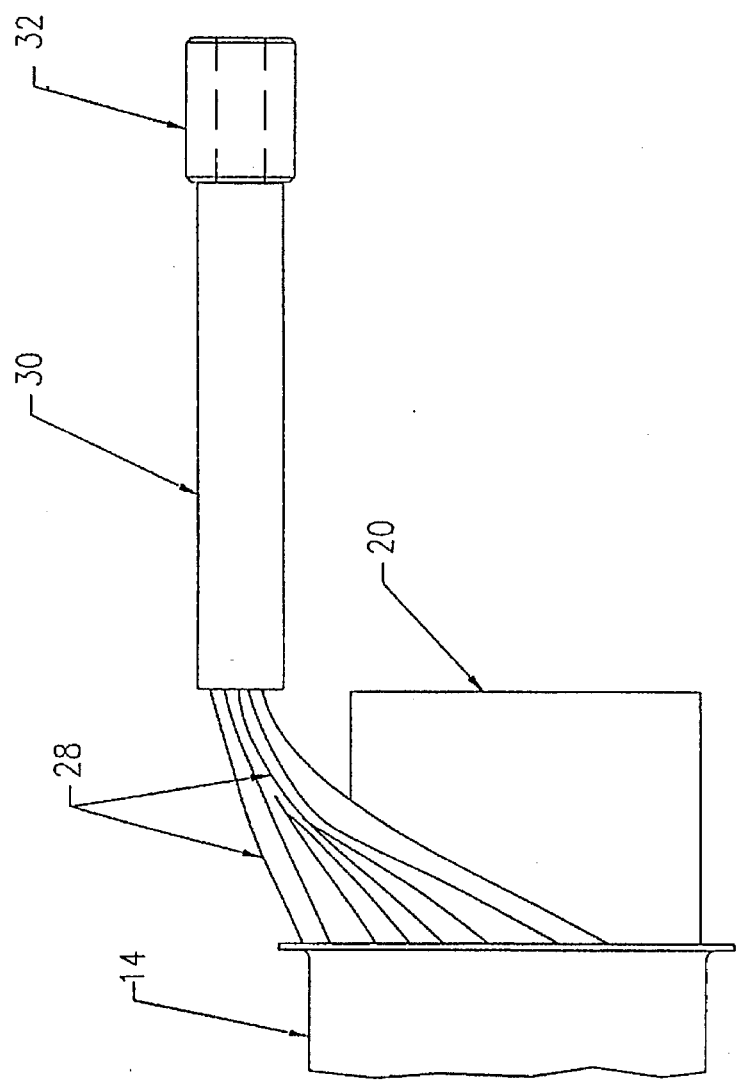
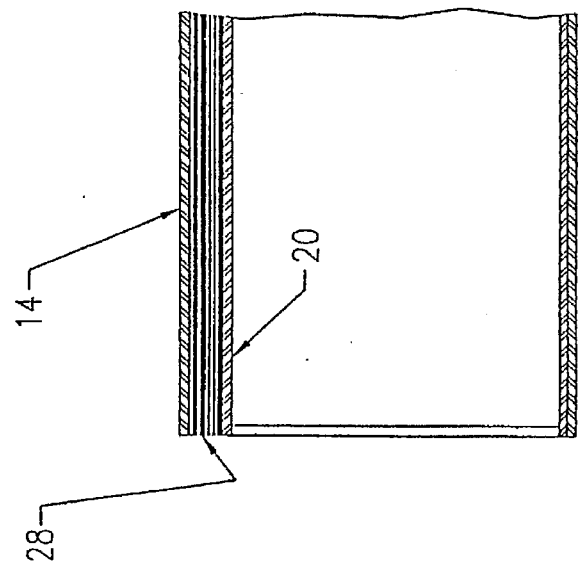
FIG. 11

ENDOSCOPE WITH POSITION DISPLAY
FOR ZOOM LENS UNIT AND IMAGING
DEVICE

PRIORITY DATA

This is a continuation-in-part of U.S. patent application Ser. No. 08/319,886, filed 7 Oct. 1994 for "Electronic Endoscope With Zoom Lens System" (Attorney Docket No. OKTA-1), now U.S. Pat. No. 5,582,576.

FIELD OF THE INVENTION

The present invention relates generally to endoscopes and more specifically to electronic image displays for endoscopes which have a solid state imaging device and an optical system that includes a zoom lens unit for transmitting images to the solid state imaging device.

PRIOR ART

Endoscopes, which are instruments used to inspect cavities or openings, have found a great number of applications in medicine and other technology. In the field of medicine, the use of endoscopes permits inspection of organs or other biological specimens for the purpose of inspecting a surgical site, sampling tissue and/or facilitating the manipulation of other surgical instruments, usually with the objective of avoiding invasive and traumatizing surgical procedures.

Older conventional endoscopes used in medicine have an objective lens unit at their distal (forward) ends which transmits an image of the area forward of the objective lens unit to the proximal (rear) end of the endoscope for viewing in an eye-piece, the image being transmitted to the eye-piece via an image forwarding means in the form of a so-called relay lens set or an optical fiber bundle unit. In more recent years, in place of the eye-piece and at least part of the image forwarding means, it has been preferred to provide a small size solid state video imaging device, such as one constituting a CCD chip, in the imaging plane of the objective lens, and applying the output of that video imaging device via a suitable electronic transmission system to a video monitor for viewing by the user. With both types of image transmitting and viewing arrangements, the surgeon can view the displayed image and use the information conveyed by that image to manipulate the endoscope and also other surgical instruments that have been inserted into the patient via another incision or opening in the patient's body. In the case of endoscopes that incorporate a solid state video imaging device, the image seen by the objective lens unit can be observed in the display provided by the video monitor with or without magnification.

An important consideration of recent attempts to provide electronic endoscopes is to maximize the extent that the surgical site is encompassed by the endoscope image seen by the surgeon (i.e., the field of view) without any substantially detrimental loss of image resolution.

As is well known, a critical requirement of surgical endoscopes scopes is that the maximum cross-sectional dimension of the endoscope must be kept quite small in keeping with the objective of avoiding invasive and traumatizing surgical procedures. However, it also is necessary that the endoscope have an illumination lumen or duct of a size that will assure adequate illumination of the surgical site being inspected. In addition it is desirable to provide an optical system in the endoscope that maximizes the extent of the surgical site that is encompassed by the image seen by the surgeon (i.e., the field of view) without any substantially detrimental loss of image resolution. In recognition of the two-fold desire to maximize the field Of view and image resolution, efforts have been made by others to provide endoscopes with a zoom lens system. Such endoscopes typically include an objective lens stage, a zoom lens stage, and a focusing lens for making certain that the image passed by the zoom lens is in focus. In the case where a solid state imaging device is used in an endoscope, the desired focus control can be achieved and maintained by shifting the solid-state imaging device along the axis of the endoscope in a direction and by an amount sufficient to achieve the desired focus control.

An example of an endoscope having a zoom lens and a movable imaging device system is disclosed by U.S. Pat. No. 4,488,039, issued 11 Dec. 1984 to Masamichi Sato et al for "Imaging System Having Vari-Focal Lens For Use In Endoscope". In essence the arrangement disclosed in U.S. Pat. No. 4,488,039 is one in which the position of the imaging device that is required to achieve proper focusing is estimated on the basis of the position of the zoom lens. However, the Sato et al endoscope is handicapped by the fact that the process of estimating is conducted "on the fly", which appears to limit the accuracy and/or response time of the system with respect to optimizing continuous focusing during movement of the zoom lens.

U.S. Pat. No. 4,488,039 suggests that the endoscope may be modified so as to make its control system capable of detecting changes in the position of the imaging device and then estimating an appropriate position for the zoom lens in order to achieve proper focusing of the sensed image on the imaging surface of the imaging device. That arrangement appears to suffer from the need to estimate the appropriate position for the zoom lens unit as the imaging device is being moved, so that the system disclosed by U.S. Pat. No. 4,488,039 does not embody a practical electrical mechanical design that is relatively inexpensive to manufacture and also is characterized by an efficient and reliable mode of operation.

The endoscope described in said copending U.S. application Ser. No. 08/319,886 embodies a zoom lens unit which is under operator control, plus a CCD imaging device which also is under operator control. As the zoom lens unit position is modified, the lens system focal plane shifts (inward or outward according to the direction of movement of the zoom lens unit) causing the image seen by the CCD imaging device to become unfocussed. Also as the object of attention in the video image varies in distance from the lens system, the position of the lens system focal plane also shifts, causing the image projection seen by the CCD imaging device to become unfocussed. Accordingly, the endoscope invention of said copending U.S. application Ser. No. 08/319,886, embodies an automatic control system (hereinafter described) which serves to capture a properly focused image. The automatic control system compensates for both focal plane shifts by automatically shifting the CCD imaging device position to track the lens system focal plane, and thereby maintain proper focus at the image-receiving surface of the imaging device. The control system requires as input parameters specified by the operator both the zoom lens setting and the distance from the lens system to the object of interest (the "object distance"). With that information (plus its knowledge of the characteristics of the lens system) the control system is able to maintain proper focus under all conditions. Thus, the operator may vary the zoom and deflect distance parameters over some predetermined allowable range of values, and expect the control system to properly adjust focus to track his or her commands.

However, particularly since the range of values which may be specified for either parameter is limited, it becomes advantageous to provide some form of information feedback from the control system to the operator to indicate the parameter values currently specified by the operator and their relationship to their respective permissible ranges. It also is useful to the operator to indicate, by some form of information feedback, that a particular parameter has been driven to a limit of its permissible range and hence may not be driven further in that direction.

SUMMARY OF THE INVENTION

The primary object of this invention is to provide an endoscope of the type described with means for generating feedback information to the operator to indicate the instantaneous position(s) of the zoom lens unit and/or the imaging device. The method and means chosen for providing the feedback information utilizes the video display means (e.g., TV monitor) which is used to display the optical image seen by the endoscope's objective lens. Preferably the video display means is used to simultaneously display a representation of both the zoom and object distance (focus) parameters, and also (at selected times) the limits of said parameters.

A further object of this invention is to provide an endoscope of the type comprising a movable zoom lens unit and a movable electronic imaging device, first and second selectively operable means for moving said zoom lens unit and said imaging device respectively, and novel means for displaying the position of said zoom lens unit and/or said imaging device.

A more specific object is to provide an electronic endoscope of the type having a zoom capability with a novel means for displaying the position of the zoom lens.

Another specific object of this invention is to provide an electronic endoscope of the type having a movable solid state imaging device with a novel means for displaying the position of the solid state imaging device.

A further object is to provide an endoscope of the type having an objective lens, a zoom lens unit for varying the effective field of view of the image transmitted by said objective lens, a solid state imaging device capable of providing an output signal representative of the image it receives from said objective lens via said zoom lens unit, an electromechanical control means for selectively changing the axial position of the zoom lens unit and/or the imaging device so as to assure that the optical image formed by the zoom lens is focused on the image-receiving surface of the imaging device, electronic display means responsive to the output signal from said imaging device for generating a visual display of the image transmitted by the objective lens, and means for causing said display means to generate an indication of the positions of said zoom lens and said imaging device in relation to predetermined end limits of the paths of movement of said zoom lens unit and said imaging device.

In the preferred embodiment of the invention, the endoscope comprises a tube in which the objective lens is mounted, means supporting said zoom lens and said solid state imaging device inside of said tube, first and second motion-transmitting means for moving said zoom lens and said imaging device respectively along the axis of said tube, whereby the spacing between said zoom lens and said objective lens and also the spacing between said zoom lens and said imaging device along the axis of said tube may be changed, a handle attached to said tube, display means for generating a display of the image seen by said imaging device, control means including manually operable switch means carried by said handle for controlling movement of said zoom lens and said imaging device by said first and second motion transmitting means, said control means being adapted to position said zoom lens and/or said imaging device so that said imaging device is substantially at the focus of said zoom lens at each position of said zoom lens, and means coupled to said display means for generating a display indicative of the positions of said zoom lens and said imaging device as they are moved between predetermined end limits. The control means comprises means for sensing the position of said zoom lens and said imaging device along the optical axis of the endoscope, a lookup table containing information as to the spacing required to be maintained between said zoom lens and said imaging device in order for the focal plane of said zoom lens to be located substantially at the image-receiving surface of said imaging device for all positions of said zoom lens system, means for accessing the data stored in said lookup table, and means for moving said zoom lens system and/or said imaging device in response to and in accordance with the accessed data.

Other objects, advantages and novel features of the invention will become more apparent from a consideration of the following detailed description when considered in conjunction with the accompanying drawings.

BRIEF DESCRIPTION OF THE DRAWINGS

FIG. 11 is a fragmentary sectional view on an enlarged scale illustrating how the bundle of optical fibers is terminated at the proximal end of the endoscope;

In the several views, the thickness and/or overall size of certain components are exaggerated for convenience of illustration. Thus, for example, the thicknesses of the inner and outer tubes and the diameter of the optical fibers identified hereinafter are not to scale in FIGS. 4, 9 and 11. Also, the same elements are identified by the same numerals in the several views.

DETAILED DESCRIPTION OF THE PREFERRED EMBODIMENT

Figure 1:
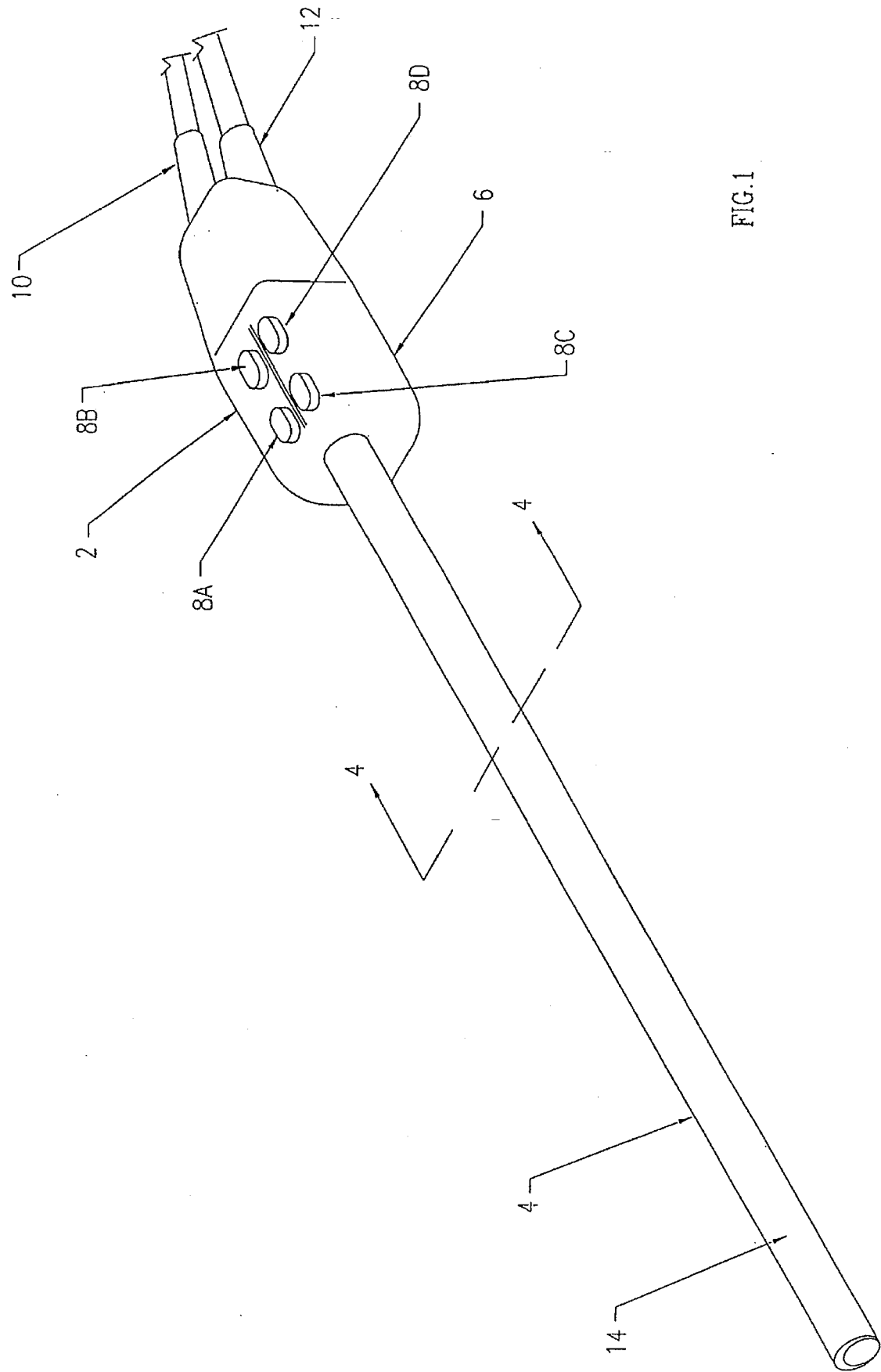
FIG. 1 is a perspective view, partially in section, illustrating a preferred embodiment of the invention.
Figure 2:
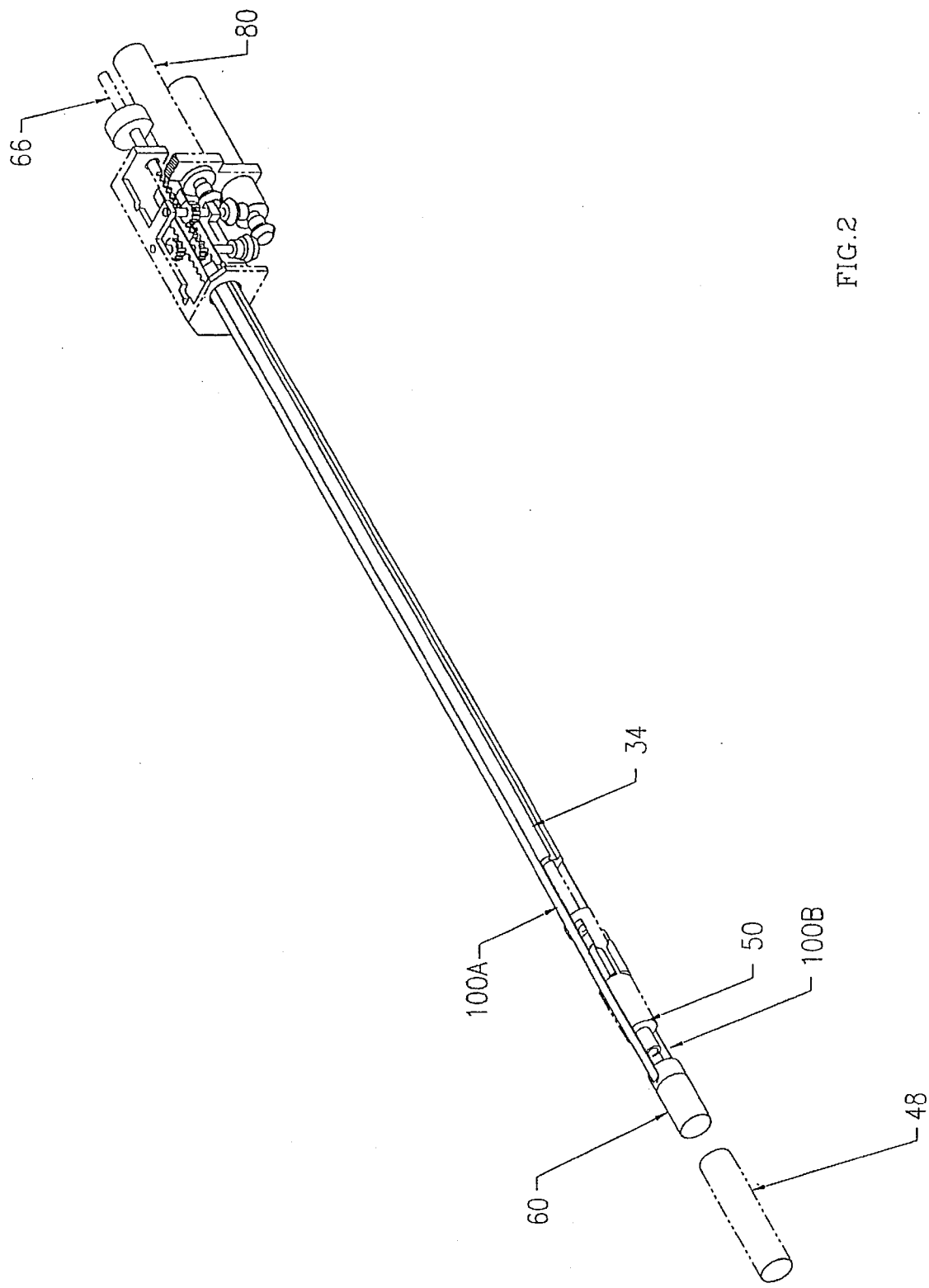
FIG. 2 is a perspective view similar to FIG. 1, with certain components removed to better illustrate the construction of the device.
Figure 8:
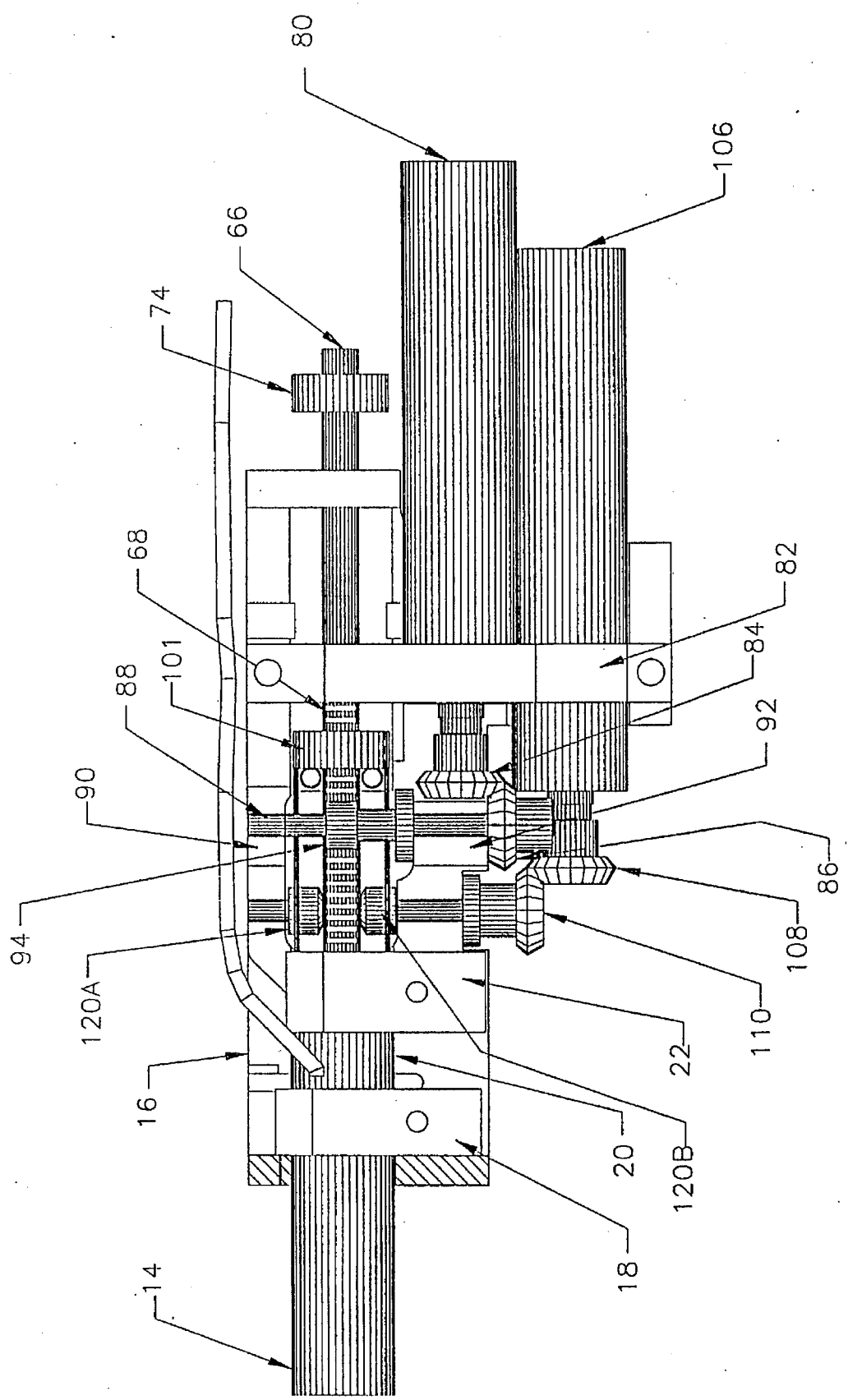
FIG. 8 is a side view in elevation further illustrating the drive trains for the zoom lens unit and the imaging device.

Referring first to FIG. 1, there is illustrated an electronic endoscope comprising a handle unit 2 and an elongate tubular assembly 4. Handle unit 2 comprises a housing 6 with openings through which four control switch buttons 8A–8D protrude. A fiber optic cable 10 and an electrical cable 12 are attached to the proximal (rear) end of housing 6. The elongate tubular assembly 4 comprises a cylindrical outer tube 14 which is open at its distal (front) end. The proximal end of tube 14 extends into housing 6 and is secured by a clamp 18 to a first portion of a mounting frame 16 (FIGS. 2 and 8). Housing 6 preferably consists of two or more mating parts that are releasably secured to one another and frame 16 by suitable screw fasteners (not shown). Mounted within outer tube 14 is a cylindrical inner tube 20 (FIGS. 4, 5 and 8) which has its distal (front) end terminating substantially in the same plane as the corresponding end of the outer tube. The proximal end of inner tube 20 extends beyond the corresponding end of outer tube 14 and is anchored by a clamp 22 (FIG. 8) to a second portion of frame 16.

Figure 4:
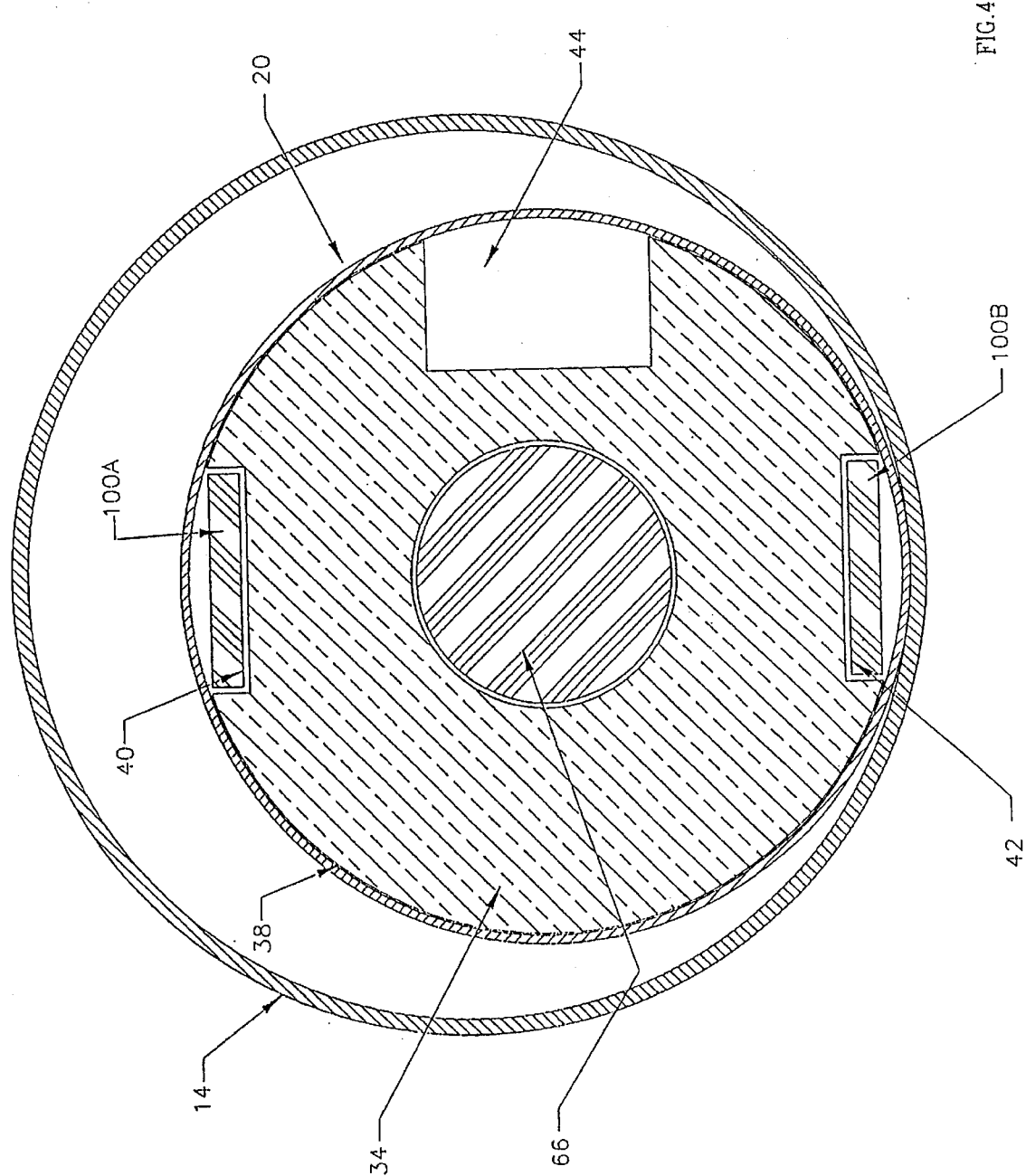
FIG. 4 is a cross-sectional view on a greatly enlarged scale taken along line 4—4 of FIG. 1.
Figure 9:
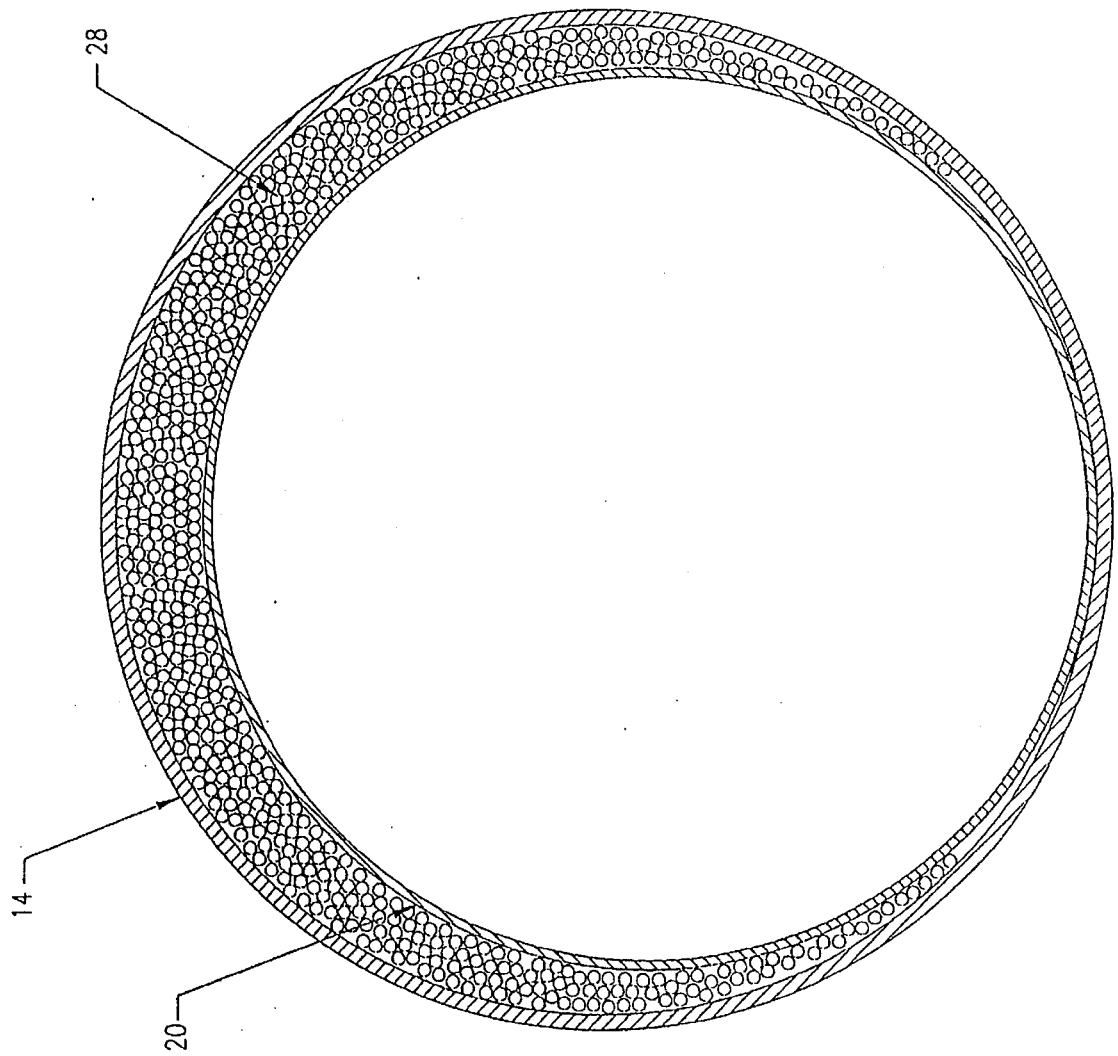
FIG. 9 is a front end view of the endoscope illustrating the disposition of the optical fibers used to illuminate, the surgical site.

As seen in FIGS. 4 and 9 the inner tube is smaller than and is mounted eccentrically to the outer tube, so as to leave a crescent shaped area to accommodate a plurality of optical fibers 28 (FIGS. 9 and 11) that are used to transmit light to illuminate the surgical site, i.e., the objective lens field of view. The distal (forward) ends of fibers 28 may (but need not) be bonded to one another by a suitable cement such as an epoxy resin; in either case, the fibers are locked in place between the two tubes, with their forward ends being optically polished and terminating substantially flush with the plane of the distal end edge of the outer tube. Fibers 28 project out of the rear end of outer tube 14 and are collected in a protective tubing 30 preferably made of a material such as a silicone rubber. The rear ends of fibers are captured in a ferrule 32 that is used to connect it to cable 10. The rear end surfaces of fibers 28 are optically polished.

Figure 5:
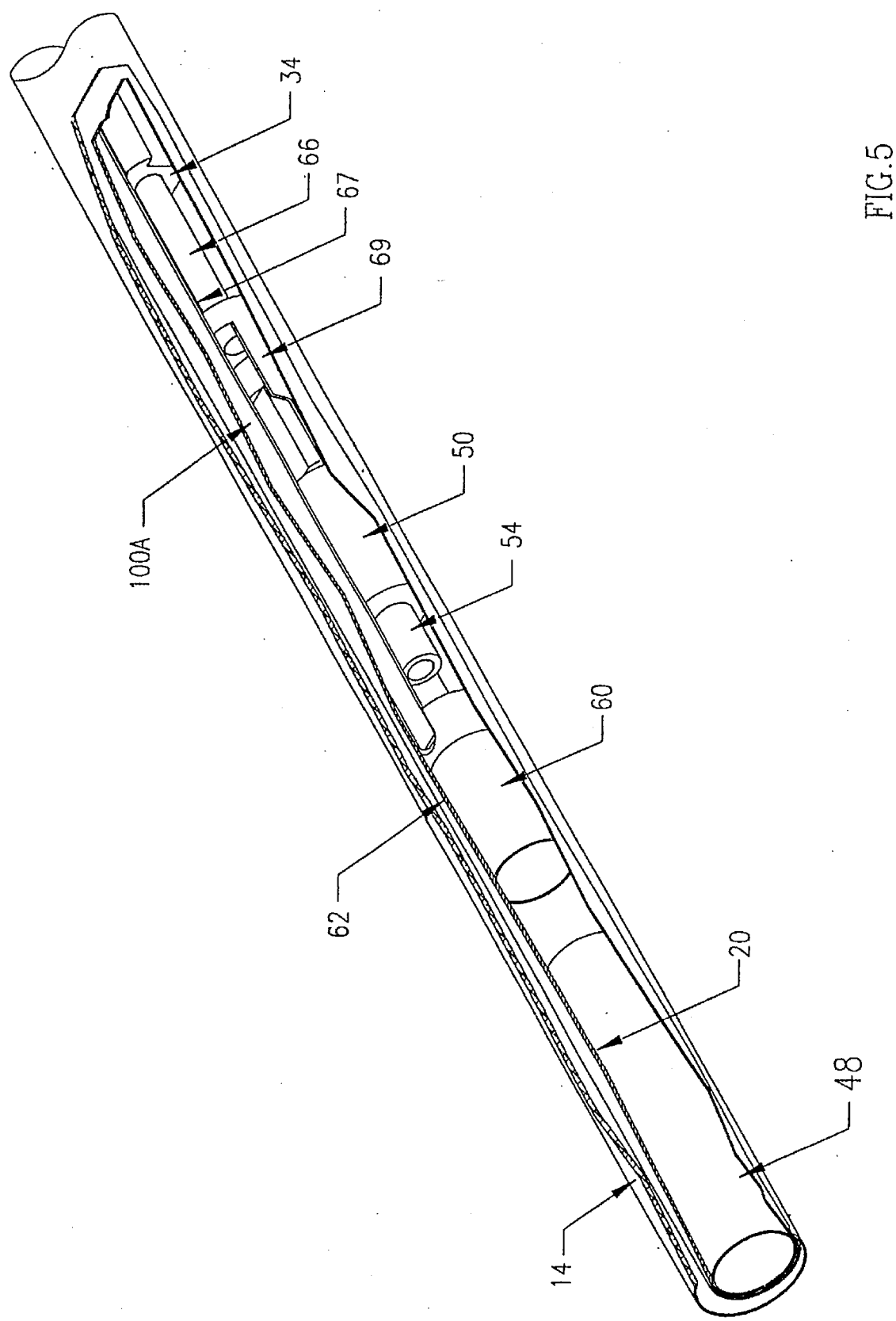
FIG. 5 is a perspective view on an enlarged scale of certain components of the endoscope, with certain components broken away.
Figure 10:
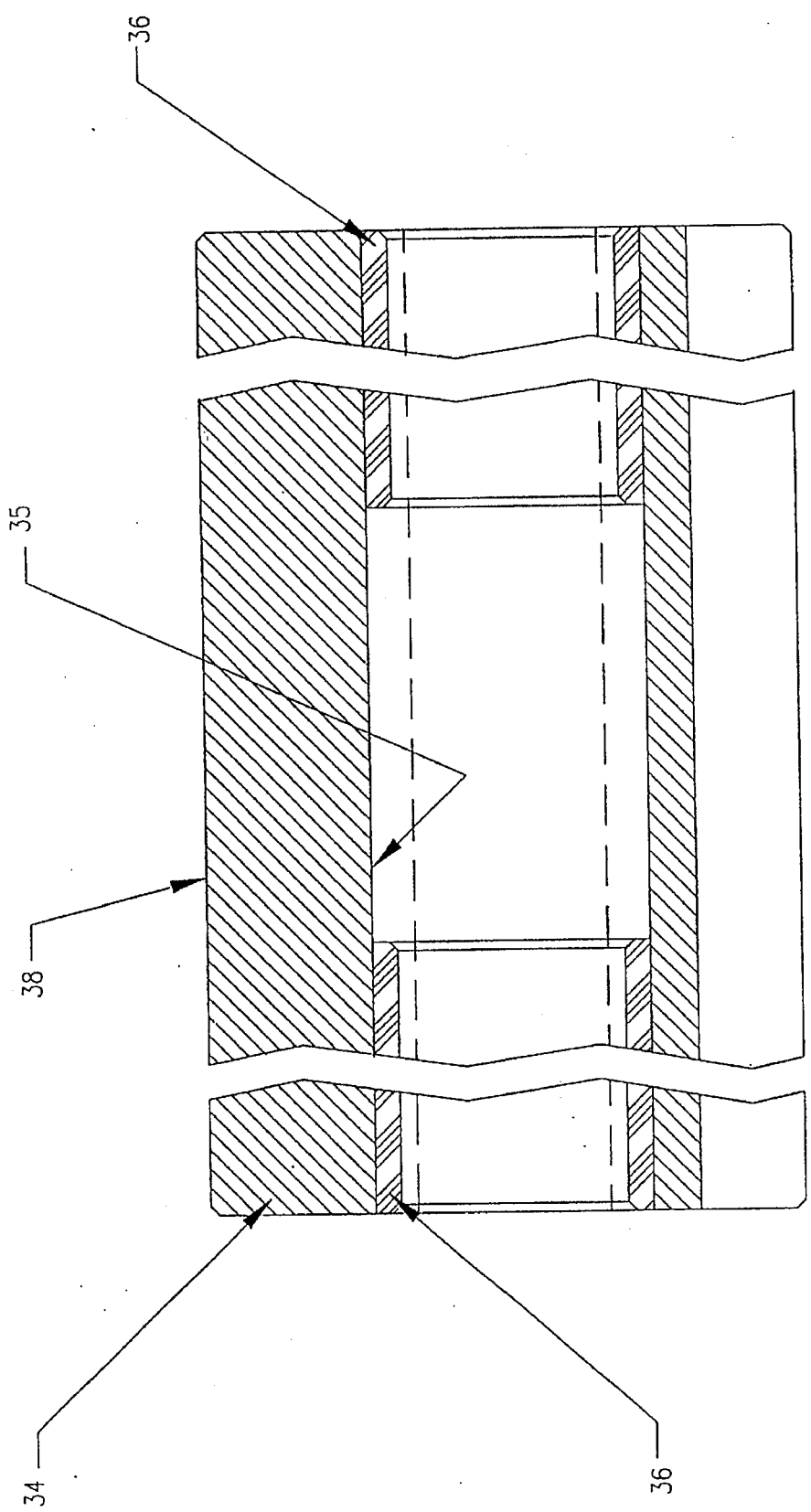
FIG. 10 is a fragmentary sectional view in elevation of the elongate bushing used to support the drive rod for the imaging device.

Referring now to FIGS. 2, 4, 5 and 10, mounted within and locked to inner tube 20 is an elongate bushing 34 that has a sleeve bearing 36 located at each end of its central bore or lumen 35 (FIG. 10). Bearings 36 are made of a material having a low coefficient of friction. The proximal (rear) end of bushing 34 terminates substantially flush with the corresponding end of inner tube 20. The forward end of bushing 34 terminates intermediate the opposite ends of tube 20 (FIG. 5). As seen in FIG. 4, bushing 34 has a generally cylindrical outer surface 38 sized so that it makes a close or tight fit with the inner surface of inner tube 20. That generally cylindrical outer surface of the bushing is disrupted by three axially extending grooves 40, 42 and 44. Grooves 40 and 42 are identical in shape and are diametrically opposed to one another, while groove 44 is somewhat deeper. The purpose of grooves 40, 42 and 44 is described hereinafter.

As seen in FIGS. 1, 2, 3, 5 and 6, mounted within the front end of and fixed to inner tube 20 is an objective lens unit 48. Details of the objective lens unit are not provided since such units are well known to persons skilled in the art. See, for example, U.S. Pat. Nos. 4,488,039; 4,491,865; 4,745,470; 4,745,471; 4,832,003; 4,867,137; and 5,122,650. However, it is to be appreciated that the objective lens unit may consist of one or more lenses. Inner tube 20 may be fitted with a separate transparent window member (not shown) disposed at its front end in front of the objective lens unit, or the front element of the objective lens unit may serve as the window.

Figure 6:
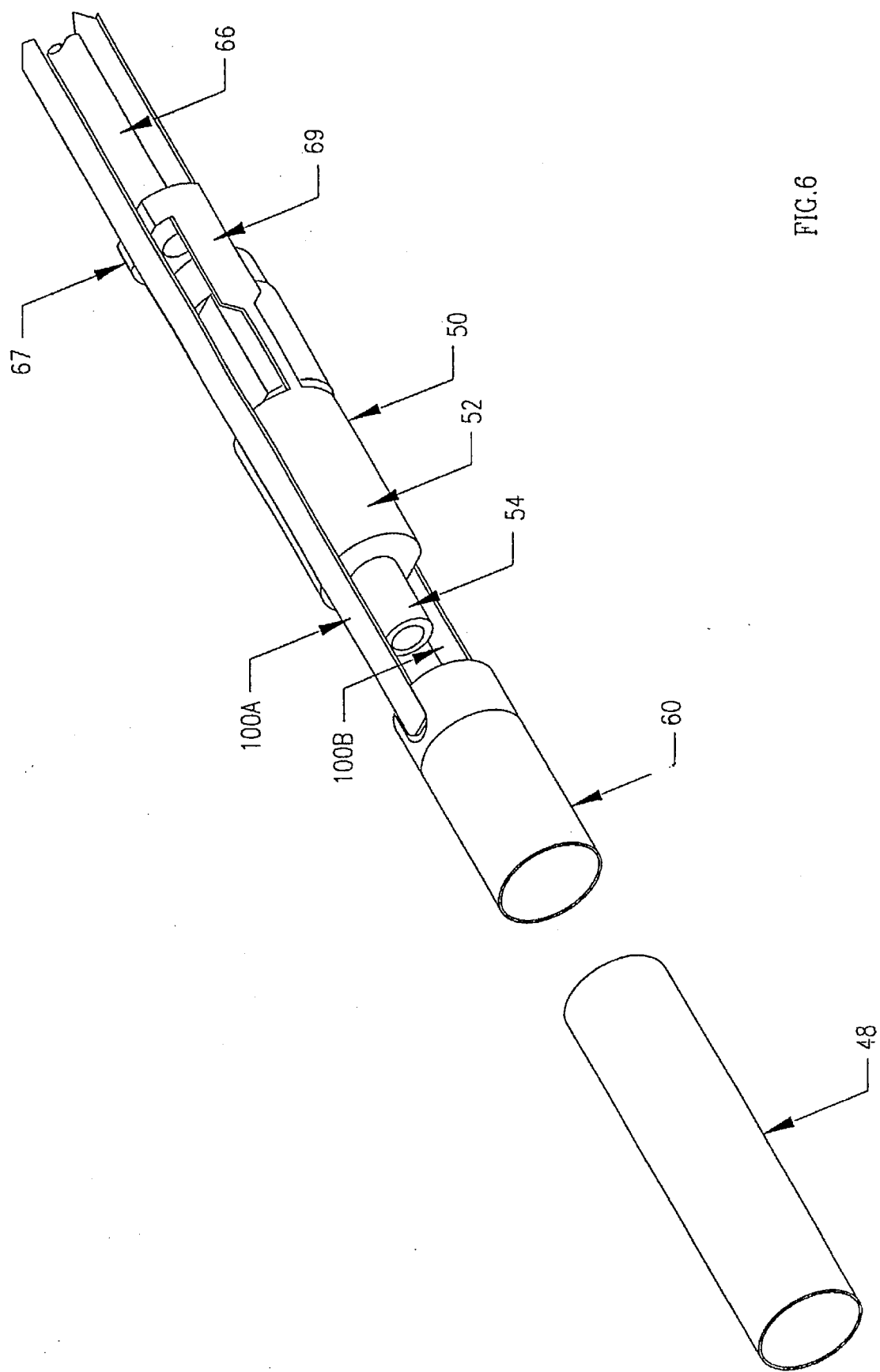
FIG. 6 is a fragmentary exploded view on an enlarged scale of certain components of the endoscope.

Also disposed within inner tube 20 is a cylindrical video imaging unit 50 (FIGS. 2, 3, 5, 6). Exact details of imaging device 50 are not illustrated since its form is not critical to the invention and instead it may take various forms, e.g., it may be like the ones described and illustrated in U.S. Pat. Nos. 4,448,039; 4,491,865; 4,867,137; and 5,166,787. Unit 50 comprises a solid state CCD semi-conductor imaging devise (not shown), preferably one comprising a CCD chip as shown in U.S. Pat. Nos. 4,756,470; 4,745,471; and 5,021,888, mounted within a cylindrical housing 52 that is sized to make a close sliding fit in inner tube 20. As seen in FIGS. 5 and 6, the forward end of housing 52 is provided with a cylindrical tubular extension 54 that serves as an aperture for the solid state imaging device. Also, although not shown, it is to be understood that the solid state CCD device has a lead frame or chip carrier with terminal pins adapted to mate with a conventional connector (not shown) on the end of a multi-strand wire cable (also not shown) that extends rearwardly in groove 44 of bushing 34 and is coupled to electrical cable 12, whereby the imaging device is coupled to external electronic circuits as hereinafter described.

Also mounted within inner tube 20 is a zoom lens unit 60 (FIGS. 2, 3, 5 and 6). Details of the zoom lens unit are not provided since its exact form is not critical to the invention and also since such units are well known to persons skilled in the art of optics (see, for example, U.S. Pat. Nos. 4,570,185 and 4,781,448). Zoom lens unit 60 may comprise one or more lenses, according to the desired zoom range and image resolution. In the preferred embodiment of the invention, the lens or lenses of zoom lens unit 60 are contained within a cylindrical housing 62 that is sized to make a close sliding fit in inner tube 20.

Separate means are provided for moving imaging device 50 and zoom lens unit 60, such means taking the form of electrically powered drive means and motion transmitting means as shown in FIGS. 2–8.

The motion transmitting means for imaging device 50 comprises a cylindrical drive rod 66 that extends through bushing 34 and makes a close sliding fit with its two end sleeve bearings 36. Rod 66 has a length sufficient for its opposite ends to project from the corresponding forward and rear ends of bushing 34 when the rod is in both its distal (forward) and proximal (rear) limit positions which are described hereinafter. Video imaging unit 50 is attached to the distal (front) end of rod 66 by a cylindrical coupling member 67 (FIGS. 3, 5, 6) that is sized to make a close sliding fit in inner tube 20. Coupling member 67 has a pair of forwardly extending, diametrically opposed arms 69 (only one of which is visible in FIGS. 5 and 6) that have their forward ends connected to the imaging unit, whereby the imaging unit will move with rod 66 when the latter is moved axially relative to inner tube 20.

Figure 3:
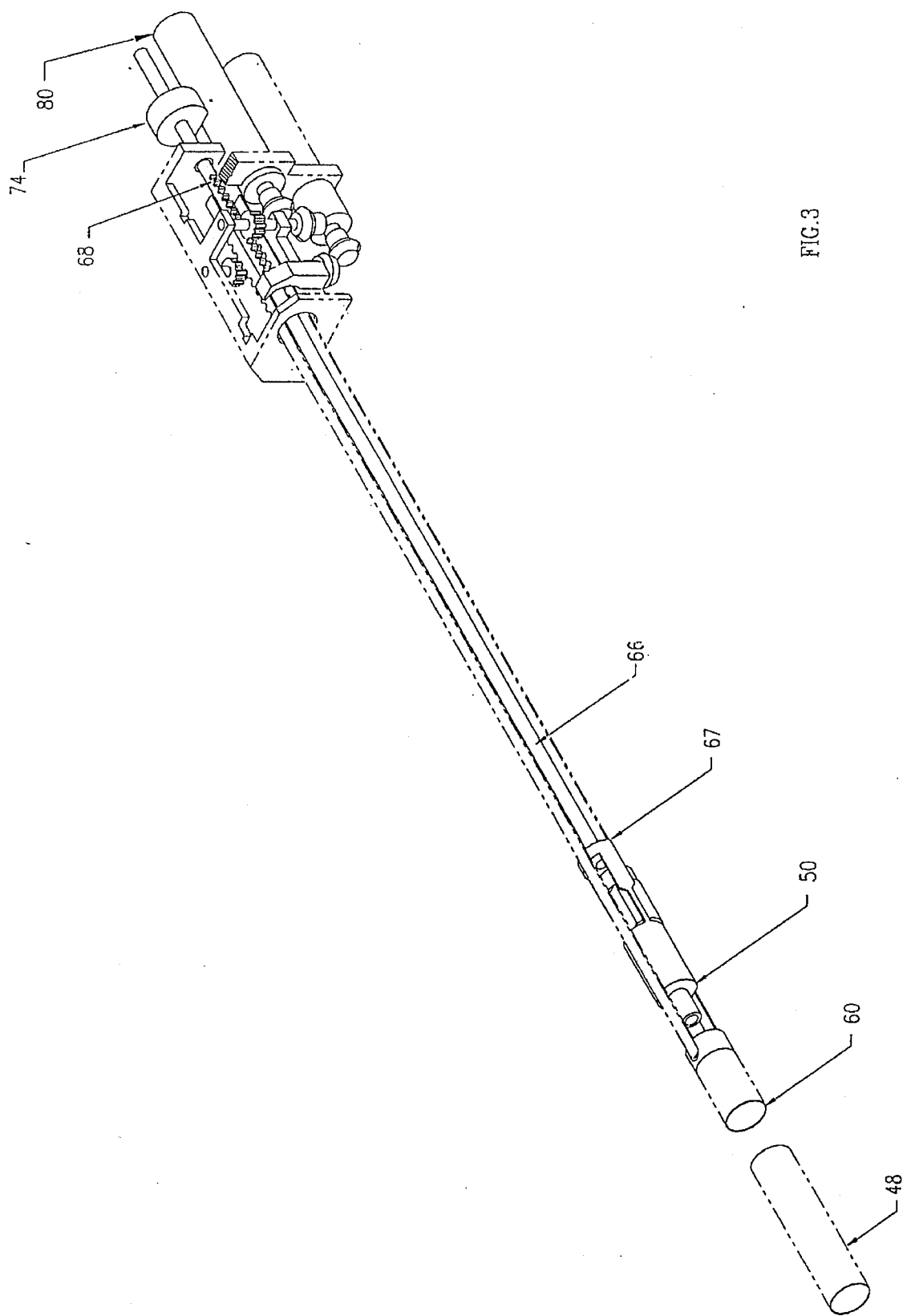
FIG. 3 is a view similar to FIG. 2, but with additional components removed to better illustrate the construction.
Figure 7:
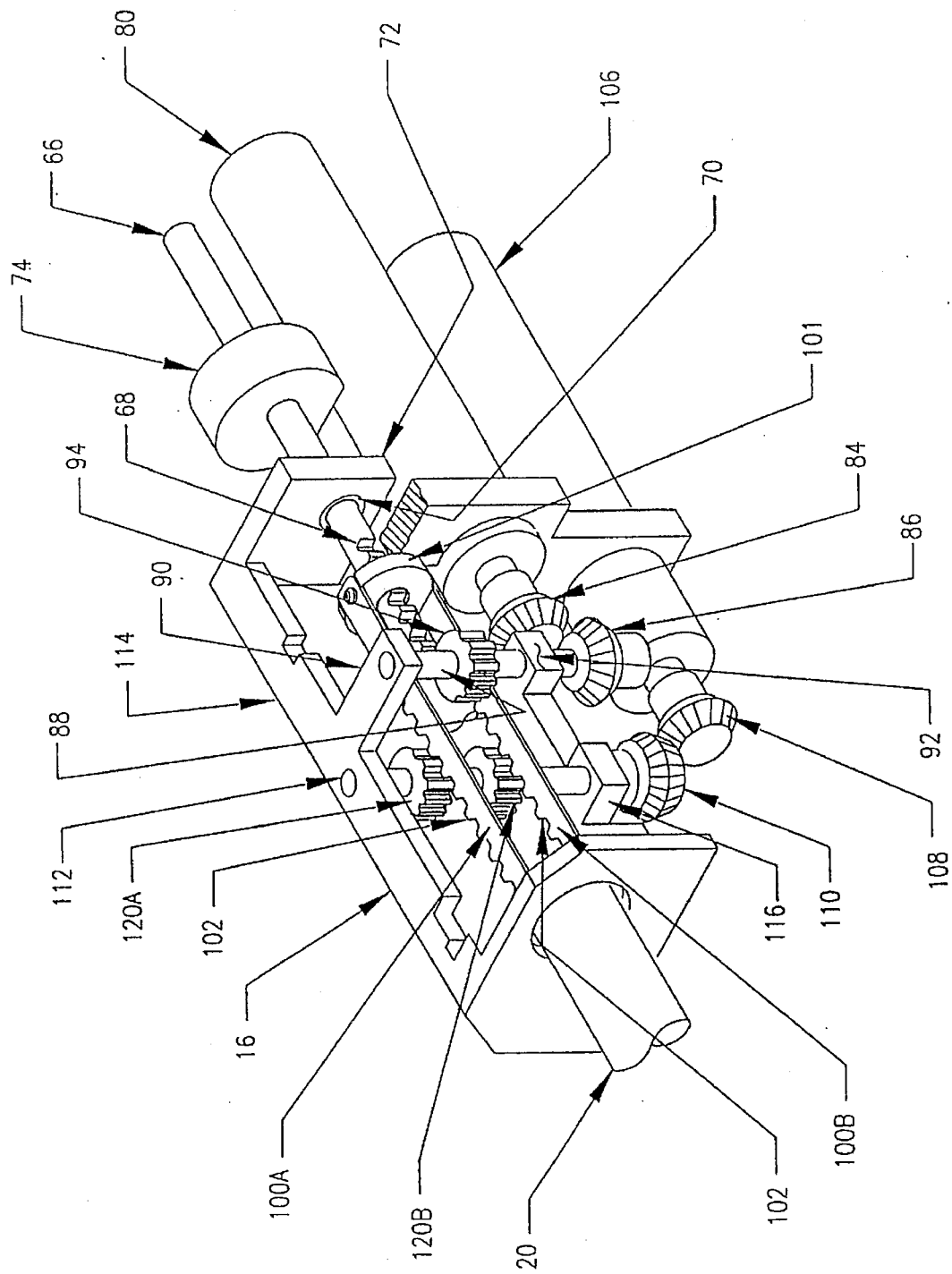
FIG. 7 is an enlarged fragmentary perspective view illustrating the drive trains for the zoom lens unit and the imaging device, with portions broken away.

As seen in FIGS. 3, 7 and 8, the proximal (rear)end of rod 66 is provided with a series of evenly spaced gear teeth 68, which permit rod 66 to function as a first gear rack. Gear teeth 68 extend over a relatively short length of rod 66 and terminate short of the proximal (rear) end of the rod. The portion of rod 66 that protrudes from the rear end of bushing 34 extends through and is slidably mounted by a bushing 70 that is mounted in a portion 72 of frame 16. Mounted on rod 66 between its proximate end and teeth 68 is a stop member 74 which is positioned to be intercepted by portion 72 of frame 16 when the rod is moved forward. Stop member 74 and frame portion 72 coact to determine a first (forward) limit position for rod 66 and imaging device 50. A second (rear) limit position for rod 66 and imaging device 50 is determined by engagement of the proximal (rear) end of imaging device housing 52 with the forward end surface of bushing 34.

The drive means for imaging device 50 comprises a reversible electrical d.c. motor 80 attached to frame 16. Motor 80 is identified hereinafter as the "focus motor" since in the invention's automatic mode of operation its function is to move imaging unit 50 so that the image-receiving surface of its CCD component is located in the focal plane of zoom lens unit 60. The output shaft of motor 80 carries a pinion gear 84 that forms part of a gear system for drive rod 66. Gear 84 meshes with a second pinion gear 86 affixed to a shaft 88 that is rotatably supported by portions 90 and 92 (FIG. 7) of frame 16. Shaft 88 in turn carries a gear 94 (FIG. 7) that meshes with teeth 68 on rod 66, whereby rotation of shaft 88 by operation of motor 80 will cause linear motion of shaft 66 and imaging device 50 in a direction determined by the direction of movement of the output shaft of that motor.

As seen in FIGS. 2 and 4–8, the motion-transmitting means for zoom lens unit 60 comprises two elongate flat rods 100A and 100B that are sized to snugly and slidably fit in grooves 40 and 42 of bushing 34. Grooves 40 and 42 have a depth that assures that rods 100A and 100B will not protrude beyond the periphery of bushing 34. The front (distal) ends of rods 100A, B are connected to housing 62 of the zoom lens unit. It is to be noted that coupling member 67 has two diametrically opposed grooves 71 (only one is shown in FIG. 6) to slidably accommodate rods 100A and 100B within tube 20. Grooves 71 are sized so as to make a close sliding fit with rods 100A, B and also so that rods 100A and 100B will not protrude beyond the periphery of coupling member 67. The rear ends of rods 100A, 100B are attached to a collar 101 that surrounds and makes a close sliding fit with rod 66. The proximal (rear) ends of rods 100A, B also are provided with a series of evenly spaced gear teeth 102 (FIG. 7).

The drive means for zoom unit 60 comprises a reversible electrical d.c. motor 106. Both it and motor 80 are attached to frame 16 by a removable clamp 82. Motor 106 is identified hereinafter as the "zoom motor". The output shaft of motor 106 carries a pinion gear 108 that meshes with a pinion gear 110 that is mounted on and secured to a shaft 112. The latter is rotatably mounted to mutually spaced portions 114, 116 of frame 16. Shaft 112 carries two axially spaced gears 120A and 120B that mesh with teeth 102 on rods 100A and 100B respectively, whereby rotation of shaft 112 by operation of motor 106 will cause linear motion of rods 100A and 100B, and thereby zoom lens unit 60, lengthwise of inner tube 20 in a direction determined by the direction of rotation of the output shaft of the motor. Axial movement of zoom lens unit 60 is limited by two separate stop means. The forward limit position is determined by engagement of collar 101 with two stop pins 103 affixed to frame 16. The rear limit position is determined by engagement of collar 101 with frame portion 72. The two mechanically-determined limit positions are set so as to permit the zoom lens unit a suitable total travel distance therebetween.

Figure 13:
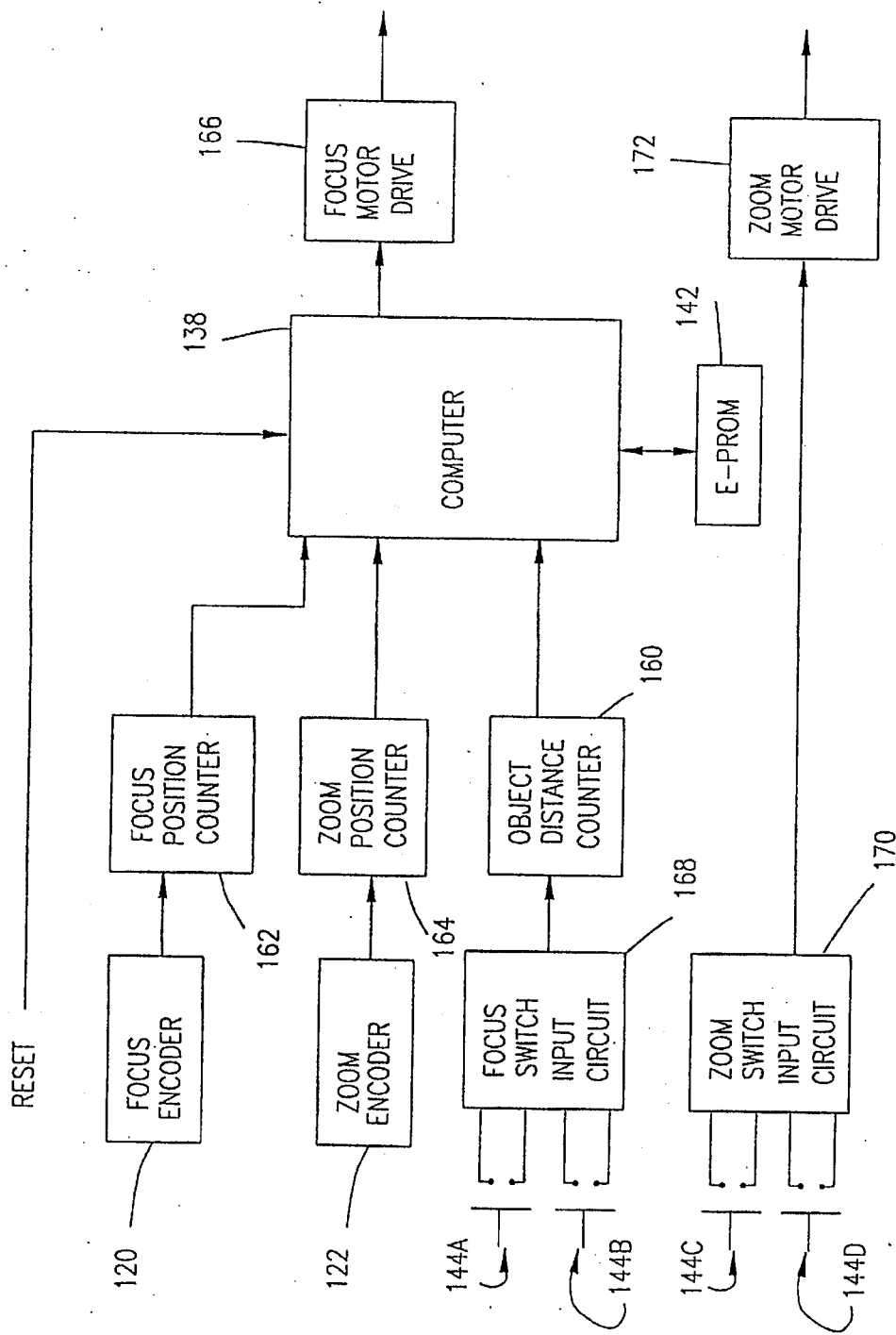
FIG. 13 is a block diagram identifying components of the control system for the endoscope, including certain components established by programming of the computer that form part of the control console.

Referring now to FIG. 13, the housings of focus motor 80 and zoom motor 106 include position-sensing encoders represented schematically at 120 and 122 that are coupled to the output shafts of the motors and are designed to provide pulse-type signal outputs that are polarized plus or minus according to the direction of movement of the output shafts of motors 80 and 106 respectively. Shaft encoders 120 and 122 may take various forms but preferably they are incremental digital encoders. Because incremental position-sensing shaft-coupled encoders are well known, details of construction of the encoders are not provided herein.

Figure 12:
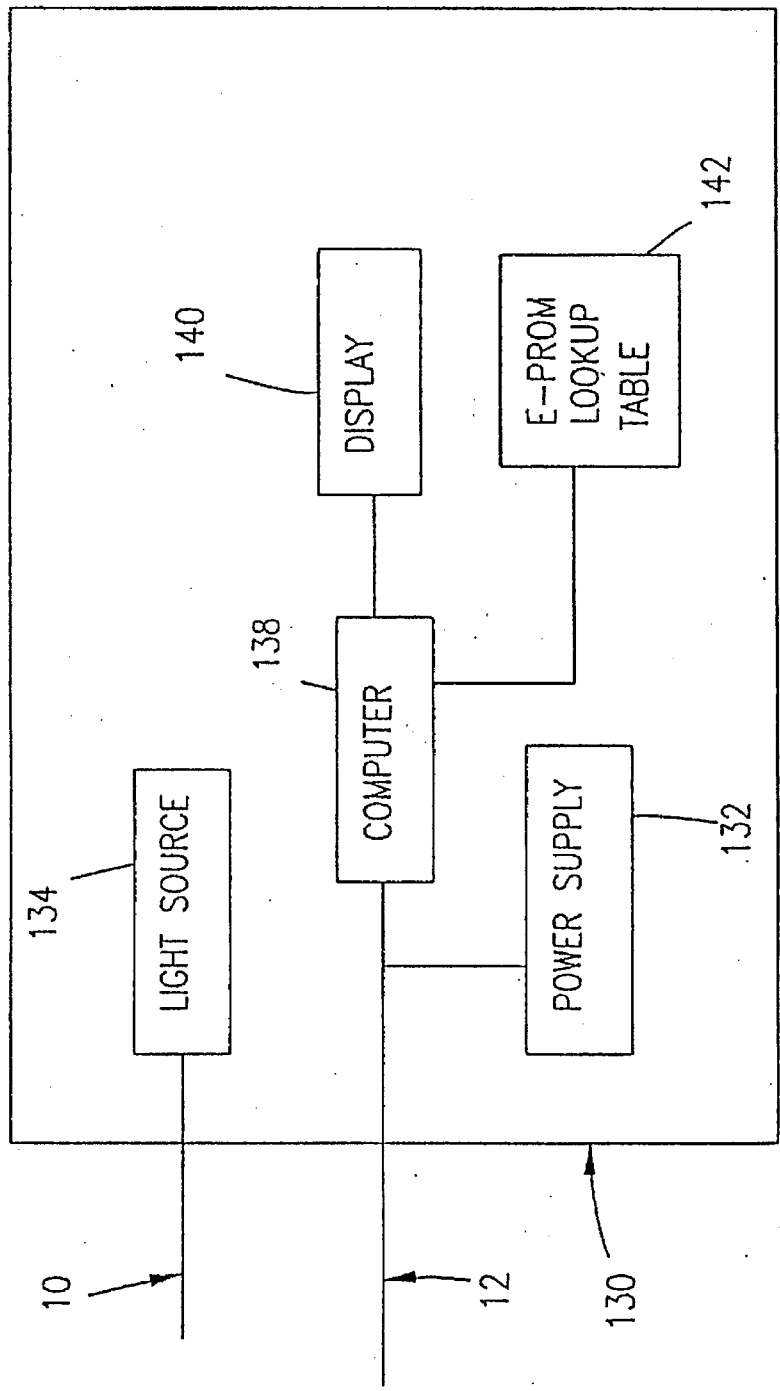
FIG. 12 is a schematic view of the electronic control console to which the endoscope of FIG. 1 is connected.

FIG. 12 diagrammatically illustrates an electronic console 130 to which the endoscope is coupled. Essentially the console comprises a light source 134 for the endoscope, an electronic controller comprising a digital computer 138 (which includes a microprocessor and associated memory, control and input and output circuits), a display module 140 that includes a CRT display device (FIG. 20) whereby the surgeon or other user may monitor the images seen by the endoscope, an electronic memory device 142, preferably but not necessarily in the form of an E-prom, that serves as a zoom/focus lookup table as hereinafter described, and a power supply 132 for the solid state imaging unit 50, motors 80 and 106, and the electronic controller. Power supply 132, light source 134, computer 138, display module 140 and E-prom 142 are interconnected as represented schematically in FIG. 12 so as to permit the mode of operation described hereinafter. Although not shown, it is to be understood that power supply 132 includes a manually operated main power switch (not shown) which is used to turn the instrument "on" and "off".

Optical fiber cable 10 is coupled to console 130 so as to be able to transmit light from light source 134 to light fibers 28, whereby when that light source is energized by operation of the controller, the resulting light beam will illuminate the objective field of view. Multi-wire cable 12 is connected at its outer end to power supply 132 and computer 138; at its inner end cable 12 has certain of its wires coupled by a connector (not shown) to terminals of the CCD chip of imaging device 50 and others of its wires connected to motors 80 and 106 and the control switches associated with buttons 8A–8D.

Referring again to FIG. 13, the switch buttons 8A and 8B form part of two focus control switches 144A and 144B, while switch buttons 8C and 8D form part of two zoom control switches 144C and 144D. Preferably, a second like set of foot-operated switches (not shown), are added in parallel with switches 144A–D so as to give the surgeon the option of controlling maneuvering of imaging device 50 and zoom lens unit 60 using one of his feet rather than one of his hands. As explained further hereinafter, operating switch 144A will energize focus motor 80 so as to cause the imaging device to move forward toward the distal end of inner tube 20, while operating switch button 144B will energize focus motor 80 so as to cause reverse movement of the imaging device. Similarly, operating switch button 144C will energize motor 106 so as to cause the zoom lens unit to move forward toward the distal end of inner tube 20, while operating switch 144D will energize motor 106 so as to cause reverse movement of the zoom lens unit. Moving the zoom lens unit forward causes the field of view seen by the imaging device to narrow while moving the zoom lens unit rearward causes the field of view to widen. It is preferred that the zoom lens unit be designed to "zoom" between a field of view of about 20 degrees to one of about 70 degrees.

Computer 138 is configured by its software program to provide an object distance counter 160, a focus/CCD position counter 162, and a zoom position counter 164. The computer is arranged to provide a control signal to a focus motor drive circuit 166 that preferably forms part of the controller 130. Switches 144A and 144B are connected to a focus switch input circuit represented schematically at 168 that provides an input to object distance counter 160, while switches 144C and 144D are connected to a zoom switch input circuit 170 that provides control signals to a zoom motor drive circuit 172.

Figure 14:
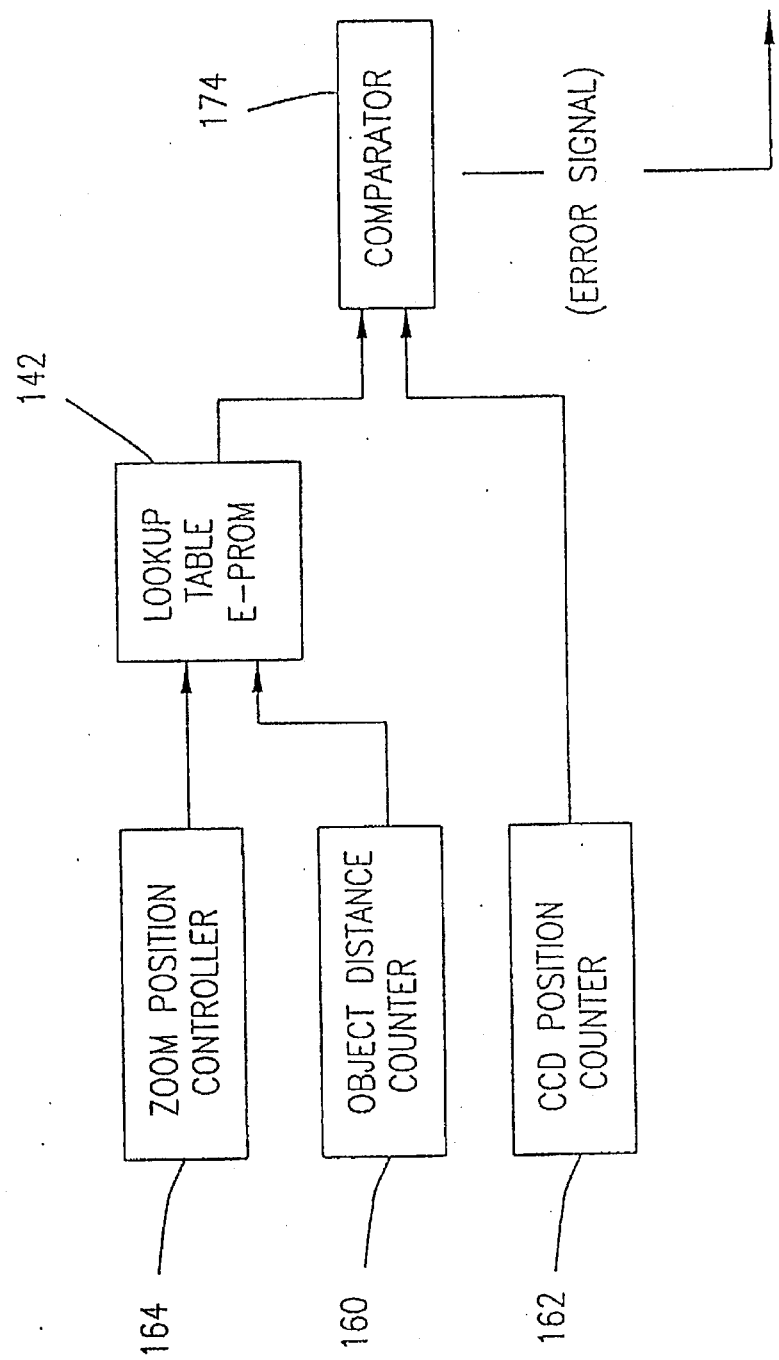
FIG. 14 is a schematic view further illustrating the control system.

Counters 162 and 164 provide outputs that permit computer 138 to determine the extent of rotation of the output shafts of motors 80 and 106 from pre-selected positions which are stored in E-prom 142, whereby at any given time the counts in the counters represent the exact positions of imaging device 50 and zoom lens unit 60 (in relation to the pre-selected reference positions along the axis of tube 20). As illustrated in FIG. 14, the computer is configured so that (1) the outputs from object distance counter 160 and zoom position counter 164 are applied to E-prom 142 to obtain a position data output signal according to those counter outputs and (2) the output signal obtained from E-prom 142 and the output of focus/CCD position counter 162 are applied to a comparator or adder 174 (established by computer programming), with the output of the comparator being an error signal that is supplied to focus motor drive 166.

Figure 15:
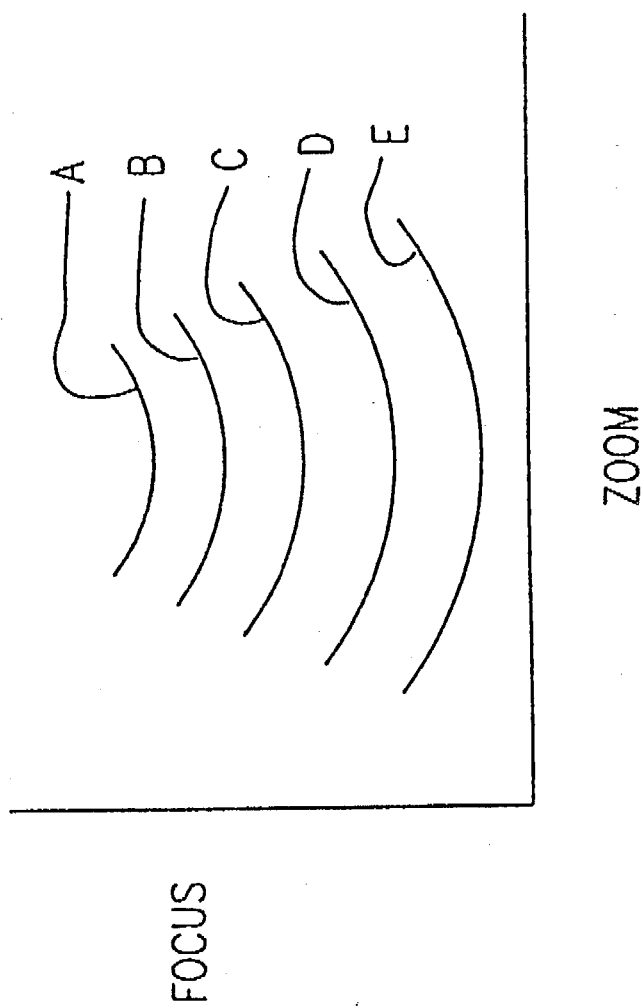
FIG. 15 illustrates the type of curves that are recorded in a lookup table that forms part of the invention.
Figure 16:
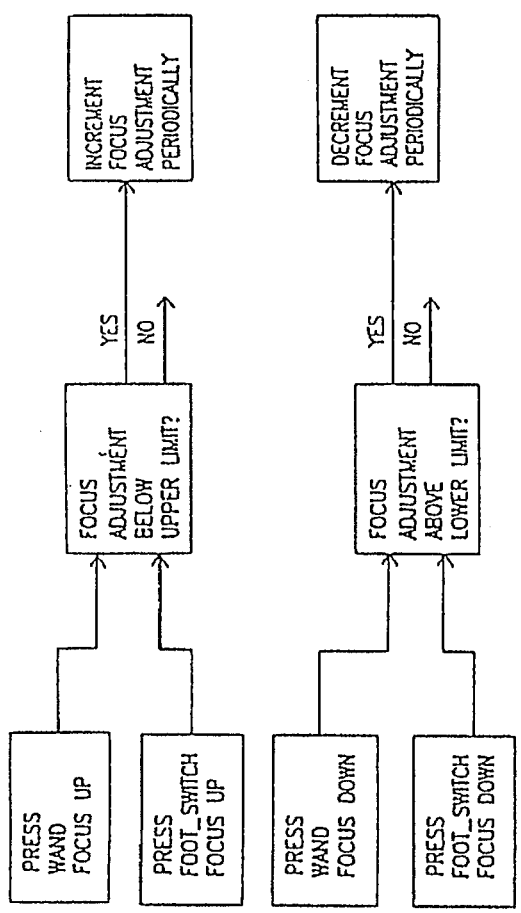
FIGS. 16–19 are flow diagrams illustrating the mode of operation established by the computer software program embodied and/or used with the controller of the endoscope.

FIG. 15 relates to the kind of data that constitutes the zoom/focus lookup in table E-prom 142. In FIG. 15, each of the curves A–E is a plot of different positions of (1) the zoom lens in relation to the objective lens ("Zoom") versus (2) the corresponding distances between the CCD imaging device and the objective lens unit ("Focus") that is required to assure that the image-receiving surface of the imaging device is in the focal plane of the zoom lens unit. Each of the curves A–E is for different object distances. As used herein, the term "object distance" means the distance measured from the objective lens to the viewed object. By way of example, the viewed object may be a human organ or other surgical site. Also by way of example but not limitation, the curves A, B, C, D and E may represent object distances of 50, 75, 100, 125 and 150 mm. respectively. Curves A–E are merely for illustration and are not intended to constitute representations of actual data stored in E-proms 142. However, specific data constituting the relative positions of the CCD imaging unit ("Focus") and the zoom lens unit ("Zoom") required to achieve correct image focusing on the CCD imaging unit for different object distances are stored in E-prom 142 and are accessed by the computer during execution of the program illustrated in FIGS. 17–20.

The data constituting the focus/zoom lookup table stored in E-prom 142 are pre-calculated according to the specific parameters of the lenses embodied in objective lens unit 48 and zoom unit 60, with such pre-calculation involving ray tracing and computer computation. No attempt is made herein to present specific data stored in the E-prom lookup table, since such data will vary with lens parameters and also since the procedure for deriving that data is well-known to persons skilled in the art.

FIGS. 16–19 are flow charts illustrating some of the software program for computer 138. Some or all Of the software program and the lookup table may be permanently installed via firmware, or may be loaded into the computer from an external storage medium at the time of use. In either case, the program is designed so that after power has been applied to the system, the operator can cause the computer to automatically execute an initializing "reset" routine that results in motors 80 and 106 shifting imaging device 50 and zoom unit 60 to predetermined positions intermediate their mechanical limits, those predetermined positions being such that the image of a viewed object will be in focus on the image-receiving surface of the CCD imaging device when the front end of the endoscope is positioned to provide an object distance value of "n" mm, "n" being an arbitrary value selected for the initializing routine.

Figure 17:
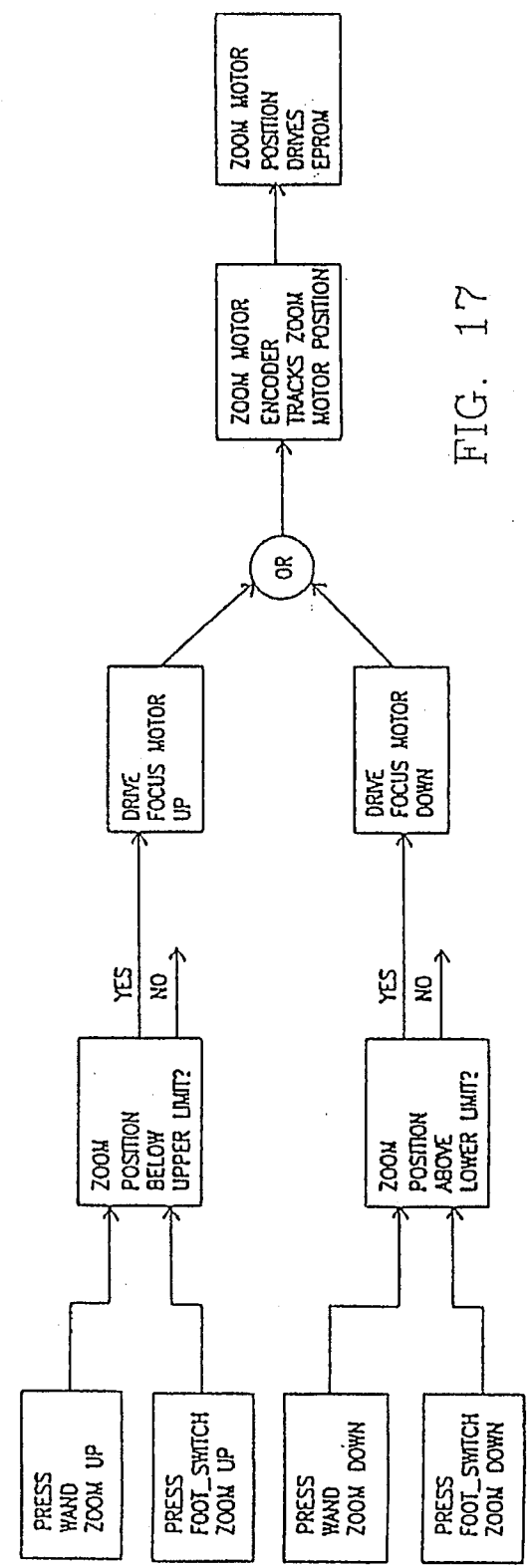
Figure 18:
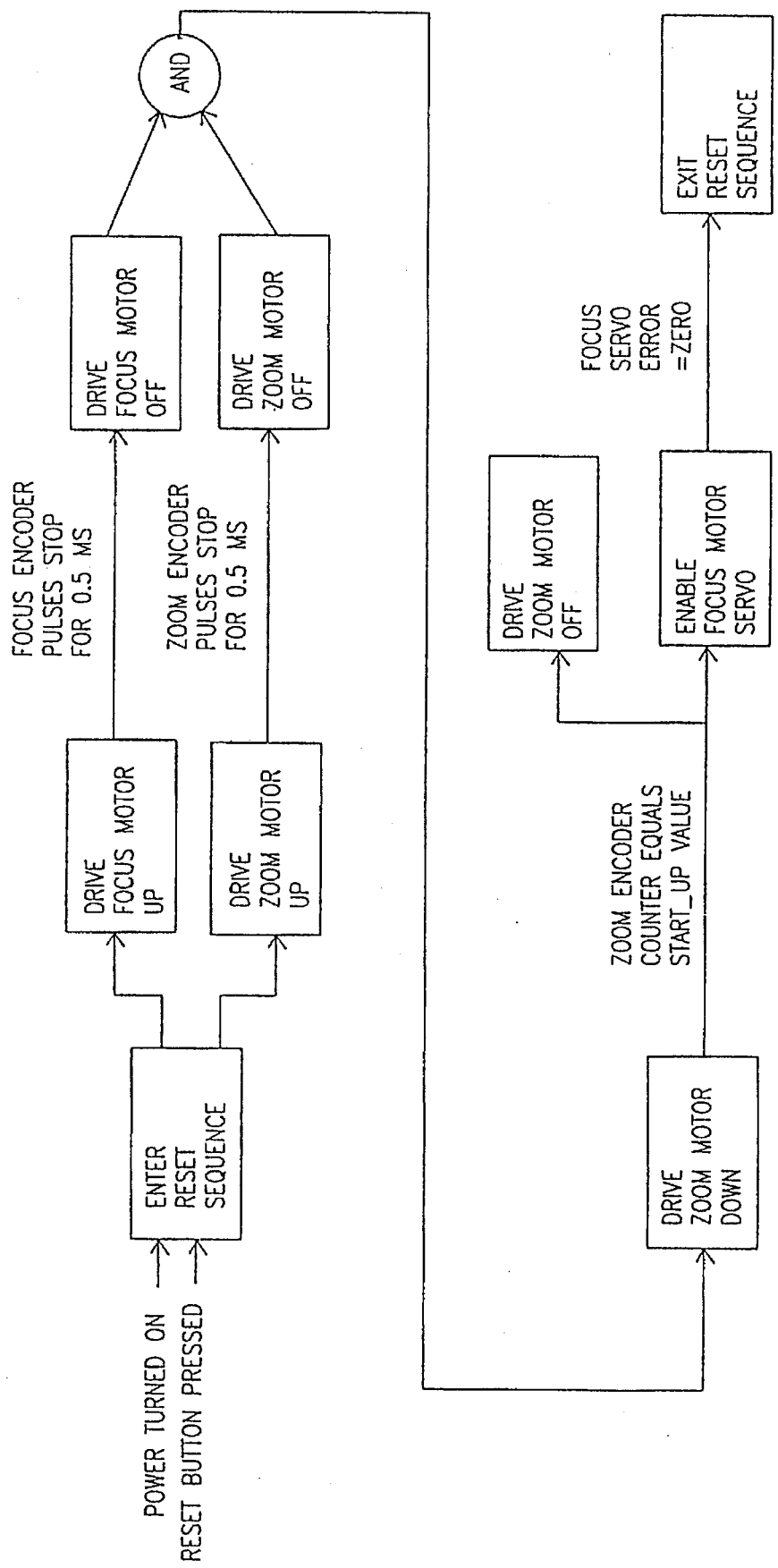
Figure 19:
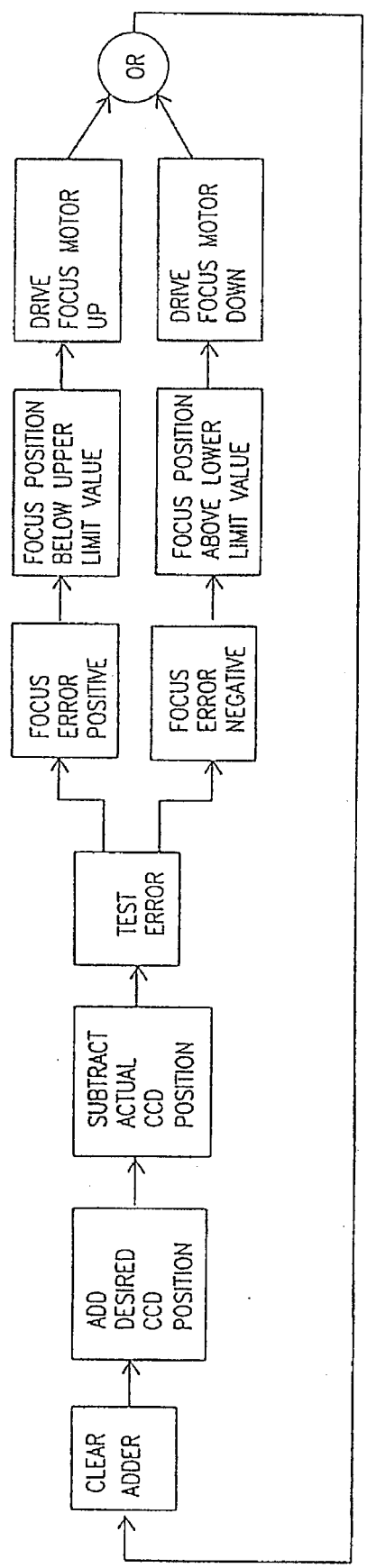

Operation of the endoscope is described hereinafter with reference to FIGS. 13–19. The control console is provided with a button-type reset switch (not shown) that is depressed by the physician or other user after the power has been turned on, thereby causing the computer to execute the aforementioned reset routine which is illustrated in FIGS. 18 and 19. That reset routine first involves operation of motors 80 and 106 so as to drive imaging device 50 and zoom unit 60 in an "UP" (forward) direction until their forward mechanical limits are reached, whereupon the mechanical load on the output shafts of the motors causes those shafts, and hence the corresponding encoders 122 and 124, to stop. Stopping of encoders 122 and 124 causes computer 138 to turn off motors 80 and 106 if no pulses have been generated by both encoders for 0.5 milliseconds ("ms").

As soon as both motors have been turned off, the computer (1) resets counters 162 and 164 to zero, (2) sets object distance counter 160 to a predetermined count "n" representing the desired initial object distance, and (3) actuates zoom motor 106 and causes it to move the zoom lens unit "Down" (rearwardly) to a predetermined start-up or reset position intermediate its distal and proximal mechanical limit positions. That start-up position is determined when the count in counter 164 equals a predetermined "start-up value" (see FIG. 18) accessed by the computer as part of the reset routine. Then motor 106 is turned off and the computer actuates focus motor 80 and causes it to move imaging device 50 in a "Down" (rearward) direction to a predetermined start-up position, the arrival at that start-up position being determined when the count in focus (CCD) position counter 162 as presented to comparator 174 matches a predetermined start-up value accessed from the E-prom 142 by the computer as part of the reset routine. At this points, the counts in counter 162 and 164 are start-up counts, whereby at any given time the control system can determine new changed positions of imaging device 50 and zoom lens unit 60 by determining how much the current counts in those counters differ from the start-up counts.

At this point, a focus motor servo control loop(FIG. 19) is activated, which control loop provides the following operation. As the imaging device 50 is moved in a "Down" direction to its predetermined start-up position, encoder 120 will generate pulses that are accumulated in counter 162. The output of object distance counter 160, preset by the computer to the predetermined start-up value "n" and the output of zoom motor position counter 164, are applied to E-prom 142 to obtain an output from the zoom/focus lookup table that has a value representing the desired imaging device position. The output from E-prom 142 (representing the desired CCD position) and the output of CCD position counter 162 (representing the actual CCD position) are applied to comparator 174. Depending on whether the actual CCD position represented by the output of counter 162 is "Up" or "Down" relative to the desired CCD position represented by the output of E-prom 142, the error signal produced by comparator 174 will be positive (+) or negative (−). If it is positive, and if the actual CCD position is below a predetermined upper limit value (the latter value is stored in the computer memory), focus motor 80 will be caused to move the imaging device in an "Up" direction. If the error signal is negative and the actual imaging device position is above a predetermined lower limit value stored in the computer memory, the focus motor will be caused to move the imaging device in a "Down" direction. In either case, the count of focus position counter output 162 will change and consequently the error signal from comparator 174 will change in value toward zero. At zero error signal value, the zoom motor will stop. Although not necessary, it is preferred for reasons of stability and accuracy, to program the focus servo control loop to periodically make a comparison in comparator 174, preferably every 20 microseconds as indicated in FIG. 19. This involves clearing the comparator (adder) at the start of each new comparison operation, as noted in FIG. 19.

At this point, if the distance between the endoscope and the viewed object ("object distance") is at the value for which the imaging device and the zoom unit are preset as a result 8f the reset routine, the image that is displayed by display device 140 will be in focus. Subsequently, if the object distance changes, e.g., as a result of the endoscope being moved, or the surgeon's point of interest is changed, the displayed image may go out of focus. In such event, the surgeon can reacquire a sharp focus by operating one or the other of buttons 8A and 8B. The resulting operation will cause counter 160 to be either increased or decreased by clocked pulses while switch 8A or 8B respectively is depressed. This changed value in counter 160 is applied to the zoom/focus lookup table, resulting in a new output value being transferred from the lookup table to comparator 174. The result is a change in the error signal output from comparator 174, which in turn is utilized by the servo control system to further operate motor 80 until the adjusted CCD position as measured by counter 162 again results in a zero error signal.

Once sharp focusing has been achieved, the image will remain in focus on the image-receiving surface of the CCD imaging device even though the operator utilizes buttons 8C or 8D to operate the zoom motor so as to zoom up or down with regard to the object being viewed. As seen in FIG. 17, the zoom motor encoder 122 tracks zoom motor position, and the output of the zoom motor encoder is used to drive the E-prom to a new output value. The new value obtained from E-prom 142 is compared with the signal output of counter 162 to modify the error signal. That error signal is then utilized in the servo-control loop to cause the focus motor to operate in a direction and for a duration sufficient to locate the CCD imaging device at a position which assures that sharp focusing of the image is achieved despite the change in field of view caused by zooming up or down.

It is to be appreciated that when its main power switch (not shown) is turned on and/or the reset switch is actuated, the control system described above will automatically set the imaging device 50 and the zoom lens unit to a preselected position which provides a predetermined field of view with sharp focusing at the CCD device of the image seen by the objective lens. Thereafter, the operator has the advantage that by depressing either of the buttons 8C and 8D, the field of view may be changed without changing the object distance between the objective lens and the object being viewed. Additionally, if the need arises to change the position of the endoscope so as to change the object distance, the operator has the option of utilizing buttons 8A and 8B to refocus the image, and also the option of utilizing buttons 8C and 8D to change the field of view without again having to utilize the buttons 8A and 8B to change the position of the imaging device in a direction to restore or maintain a sharp image for viewing on displaying device 140.

Figure 20:
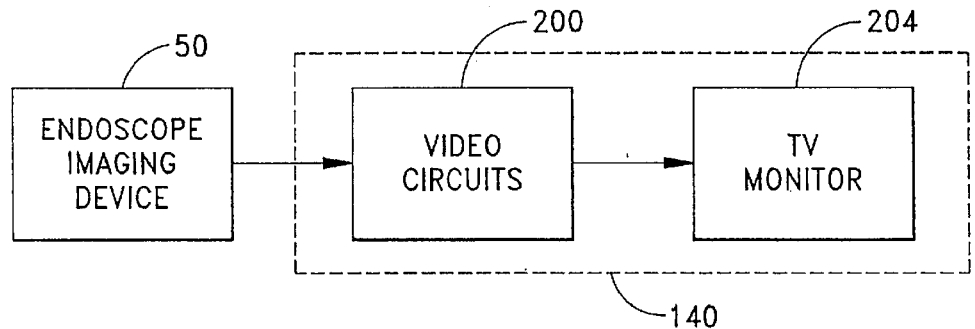
FIGS. 20–28 illustrate the means provided according to this invention for generating position marker displays.

FIG. 20 generally illustrates in diagrammatic form a system for providing an electronically generated display of the optical image that is passed by the objective lens unit 48 and zoom lens unit 60 to imaging device 50. An endoscope video signal derived from imaging device 50 is processed by conventional video circuits identified generally at 200 to provide signals that are applied to a TV monitor 204 so as to cause the latter to reproduce as a TV image the optical image seen by the endoscope's objective lens unit. The video circuits 200 and the circuits hereinafter described are preferably embodied in display module 140 (FIG. 12). The signal processing video circuits may take various forms known to persons skilled in the art and do not constitute part of the present invention. Suffice it to say that the optical image is reproduced with a magnification and field of view determined by the position of the zoom lens unit and a focusing accuracy determined by the position of imaging device 50 along the endoscope's optical axis.

Turning now to FIGS. 21 to 28, the present invention involves provision of means for generating video image markers ("indicators") that provide the surgeon with an indication of the instantaneous zoom and focus settings as well as the maximum and minimum zoom and focus settings. When focus control button 8A or 8B is operated, two vertically spaced rectangles are created on the TV monitor screen, one representing the instantaneous setting of the imaging device (focus display) and the other representing the instantaneous setting of the zoom lens unit (zoom display). The same markers are displayed if either of the zoom control buttons 8C and 8D are depressed. For convenience, these rectangular markers representing instantaneous settings are identified as "bar-graph displays" in recognition of the fact that they move horizontally in synchronism with movement of the imaging device and the zoom lens unit so that their horizontal positions provide an indication of the instantaneous positions of the imaging device and the zoom lens unit. Additionally, as the imaging device and the zoom lens unit approach either of their end limits of travel, i.e. their maximum or minimum limits, the display control system additionally generates a limit position marker in the form of an additional rectangular display The instantaneous rectangular position display markers are displayed only when one of the control buttons 8A-8D is operated and for a brief period after the button has been released, and a maximum or minimum limit marker is generated only as the imaging device or the zoom lens unit, as the case may be, approaches its maximum or minimum limit position respectively The maximum and minimum limit markers are extinguished at the same time as the instantaneous position markers.

Figure 21:
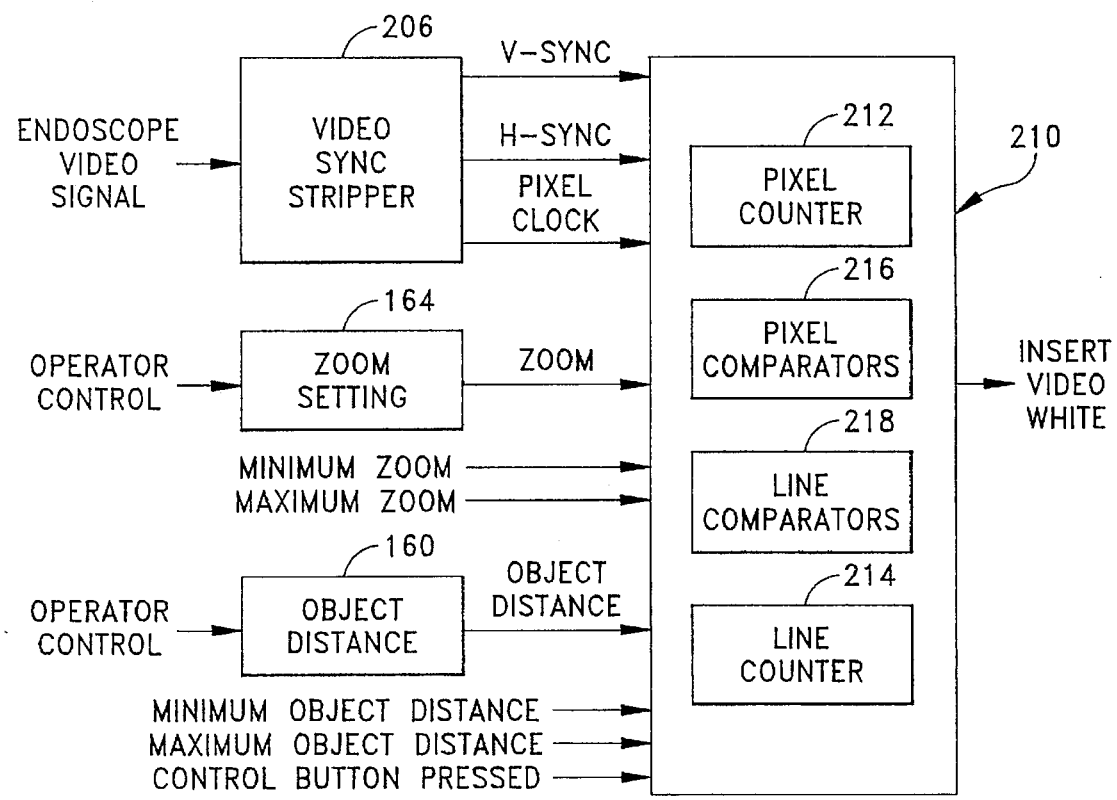

As represented in FIG. 21, the system for generating and controlling the position and limit marker displays comprises a video sync stripper circuit 206 which recovers or develops from the endoscope video signal output of imaging device 50 a vertical sync signal (V-Sync), a horizontal sync signal (H-Sync), and also a clock signal identified hereinafter as a "pixel clock". Those signals are applied as input signals to marker display control circuits, identified generally by numeral 210 which include inter alia, a pixel counter 212, a line counter 214, and pixel and line comparators 216 and 218. Also supplied as inputs to the marker display control circuits are operator-controlled zoom and object distance signals. The zoom and object distance signals are the outputs of the zoom position counter 164 and object distance counter 160 shown in FIG. 13. The output from counter 164 is the zoom magnification setting in the form of a digital value while the output from object distance counter 164 is the object distance setting in the form of a digital value. Additional inputs to the marker display control circuits are two zoom-related signals identified as "Minimum Zoom" and "Maximum Zoom", two object distance-related signals identified as "Minimum Object Distance" and "Maximum Object Distance", and a "Control Button" signal that is generated whenever any one of the control buttons 8A–8D is depressed.

Figure 22:
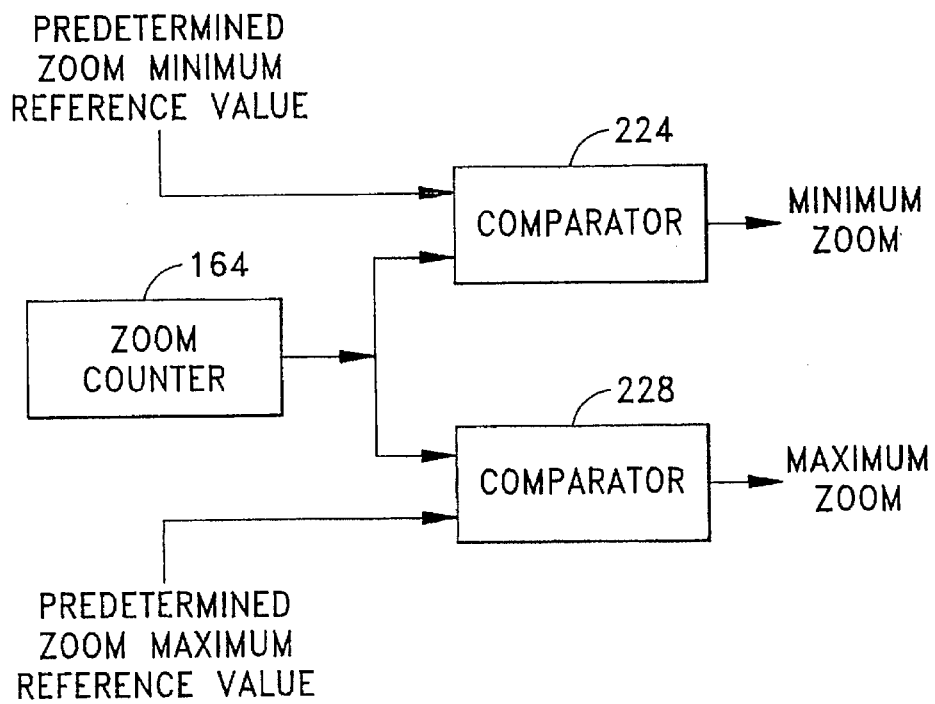
Figure 23:
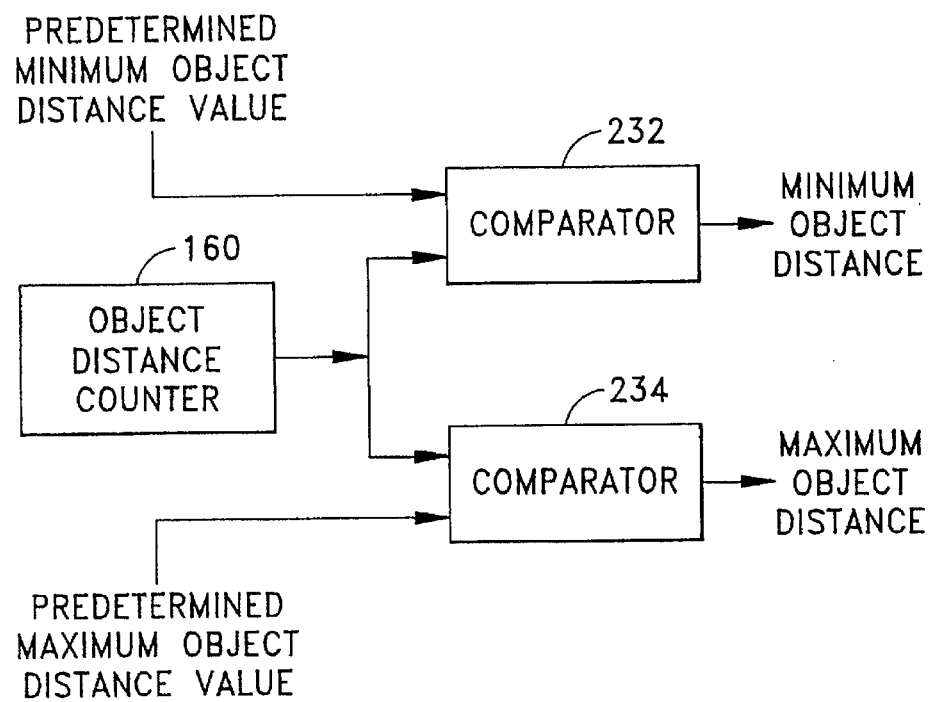

FIGS. 22 and 23 illustrate how the minimum and maximum zoom and object distance signals are generated. In FIG. 22, the signal output from zoom position counter 164 is applied to two comparators 224 and 228. Predetermined maximum and minimum reference value signals are applied as second inputs to comparators 224 and 228 respectively. When the count from zoom position counter 164 equals the predetermined minimum reference value, comparator 224 will produce the "Minimum Zoom" signal. A "Maximum Zoom" signal is generated whenever the zoom count from counter 164 equals the predetermined maximum reference value.

FIG. 23 shows a similar circuit arrangement for generating the "Minimum Object Distance" and "Maximum Object Distance" signals, with the object distance signal input to comparators 232 and 234 constituting the output from object distance counter 160 (FIG. 13), and the second input to those comparators comprising predetermined minimum and maximum reference values.

Figure 24:
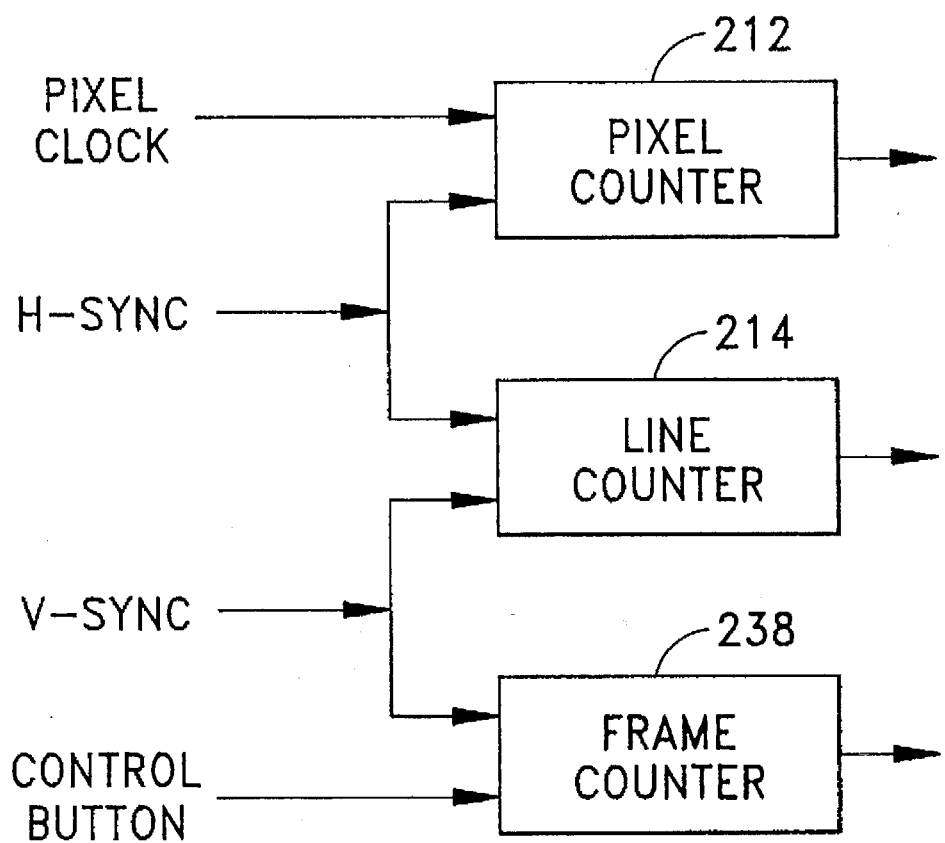
Figure 25:
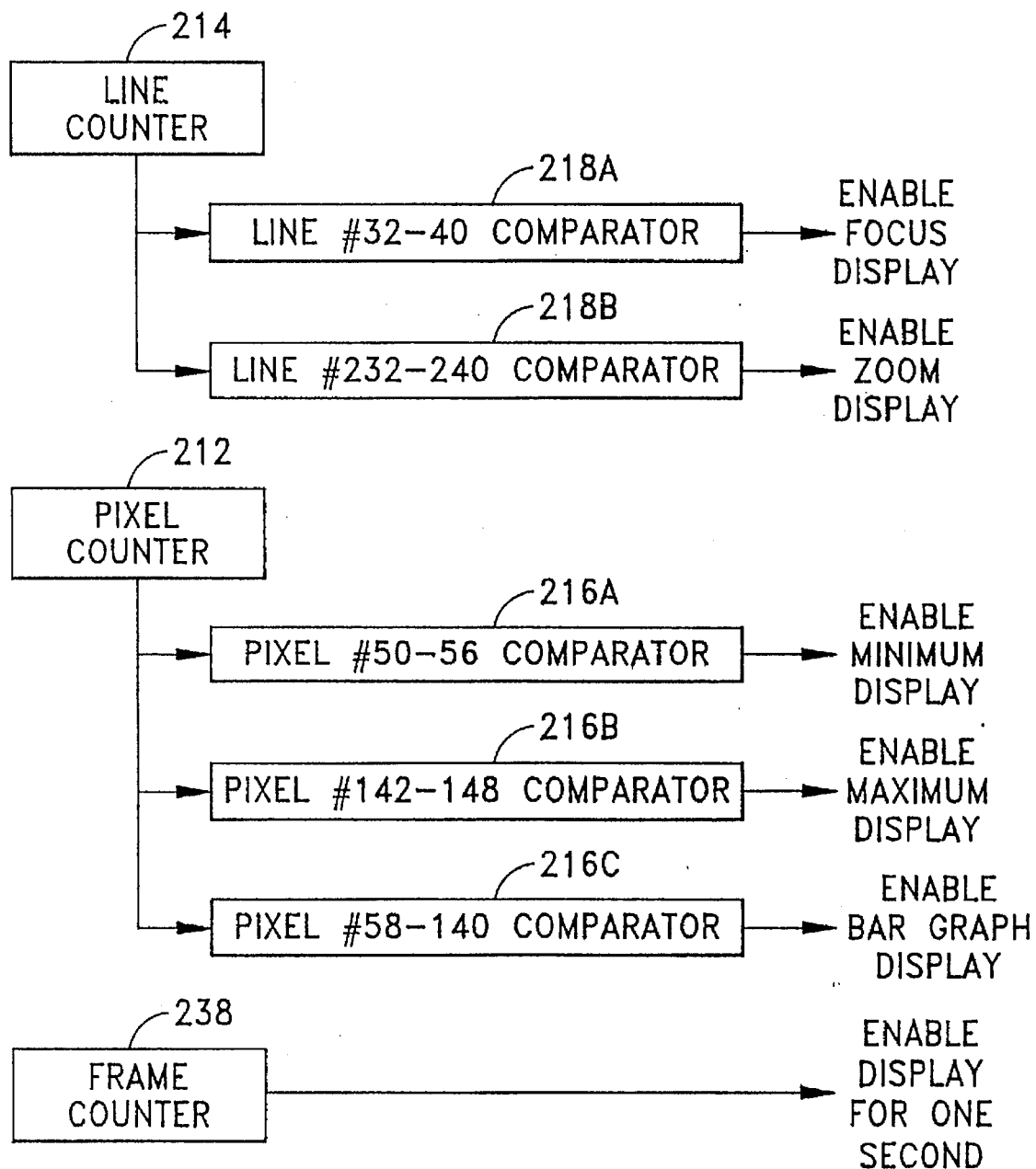

Turning now to FIGS. 24 and 25. The V-Sync and H-Sync signals are applied as inputs to raster line counter 214, the H-Sync and pixel clock signals are applied as inputs to pixel counter 212, and the V-Sync signal and the control button signal are applied as inputs to a frame counter 238. The line counter 214 counts H-Sync pulses and is initialized to zero by the V-Sync signals. The pixel counter 212 counts Pixel Clock pules and is initialized to zero by the H-sync. The frame counter 238 is initialized to zero by pressing any of the control buttons 8A–8D and counts V-Sync pulses after the pressed control button is released.

The output of line counter 214 is applied as an input to two separate line comparators 218A and 218B. Comparator 218A is adapted to produce an "Enable Focus Display" signal whenever the line count is equal to 32 or 40 or is at an in-between value. Comparator 218B is adapted to produce an "Enable Zoom Display" signal whenever the line count is equal to 232 or 240 or is at an in-between value. Both the zoom and focus indicators (markers) are displayed when any control button is pressed. Additionally, the system is arranged so that the markers continue to be displayed for one second after the depressed control button is released. The latter action is achieved by means of frame counter 238, the latter being adapted to count frames (i.e., V-Sync pulses), for the duration of one second. In this connection it is to be understood that preferably the V-Sync pulses are generated at a 60 cycle rate, and that frame counter 238 is arranged so as to generate an output signal when it has counted 60 V-Sync. pulses. The resulting output signal is identified as the "Enable Display For One Second" signal.

The output of pixel counter 212 is applied to three different comparators 216A, 216B, and 216C. Comparator 216A produces an "Enable Minimum Display" signal when the pixel counter has a count between 50 and 56; comparator 216B produces an "Enable Maximum Display" signal when the pixel count has a count between and including 142 to 148, and comparator 216C generates an "Enable Bar-Graph Display" signal whenever the pixel counter has a count in the range of 58–140.

Figure 26:
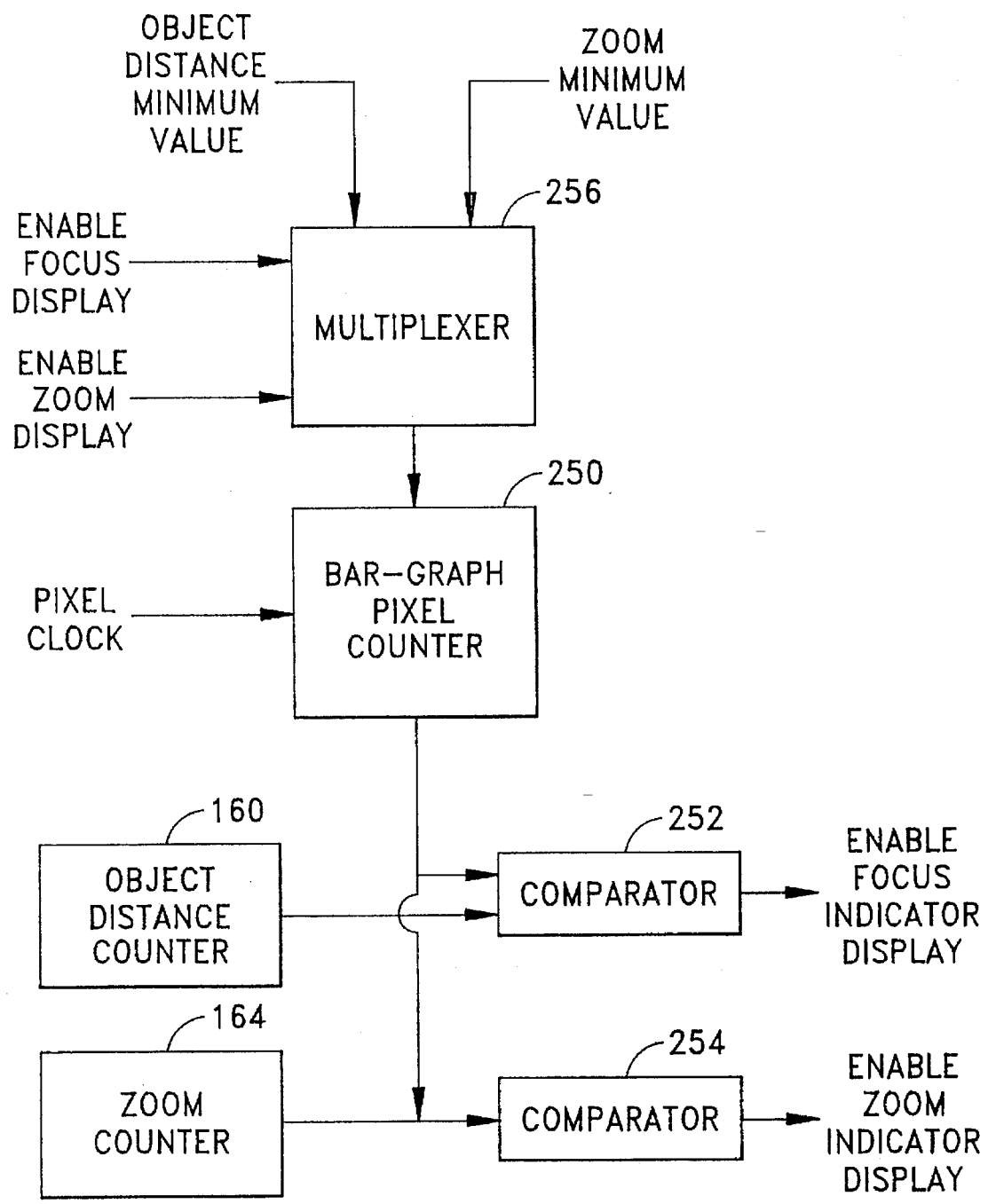

FIG. 26 illustrates how the system also is designed to produce two control signals identified as "Enable Focus Indicator Display" and "Enable Zoom Indicator Display". The means for producing these control signals comprises a bar-graph pixel counter 250, two comparators 252 and 254, and a multiplexer 256. The bar-graph pixel counter 250 is clocked by the pixel clock pulses derived from the endoscope video signal. Predetermined initial minimum values for zoom and focus are applied sequentially to the bar-graph pixel counter according to the line count. This is accomplished by applying predetermined object distance minimum value signals and zoom minimum value signals inputs to multiplexer 256, with the latter being controlled by application of the "Enable Focus Display" signal and the "Enable Zoom Display" signal produced by line comparators 218A and 218B, respectively. When the line counter has a value in the range of 32–40, multiplexer 256 is switched by the "Enable Focus Display" signal so as to pass the predetermined object distance minimum value signal to bar-graph pixel counter 250, thereby causing the latter to be preset to the minimum object distance value. When the line count is 232–240, multiplexer 256 is switched by the "Enable Zoom Display" signal so as to pass the predetermined zoom initial minimum value signal to counter 250 so as to preset the counter to that minimum value.

Comparators 252 and 254 also receive the outputs of object distance counter 160 and zoom position counter 164. When the output from object distance counter 160 matches the output of bar-graph pixel counter 250, comparator 252 will produce the "Enable Focus Indicator Display" signal. The "Enable Zoom Indicator Display" signal is generated when the signal from zoom counter 164 matches the value of the output of bar-graph pixel counter 250.

As shown in FIGS. 27A to 27F, the invention further comprises six "AND" gate output circuits that cause the several indicators (markers) to be displayed on the monitor screen. For this preferred embodiment each output AND gate circuit generates an "Insert Video White" signal that is applied to video monitor 204 so as to cause the latter to display a white marker on its screen.

Figure 27A:
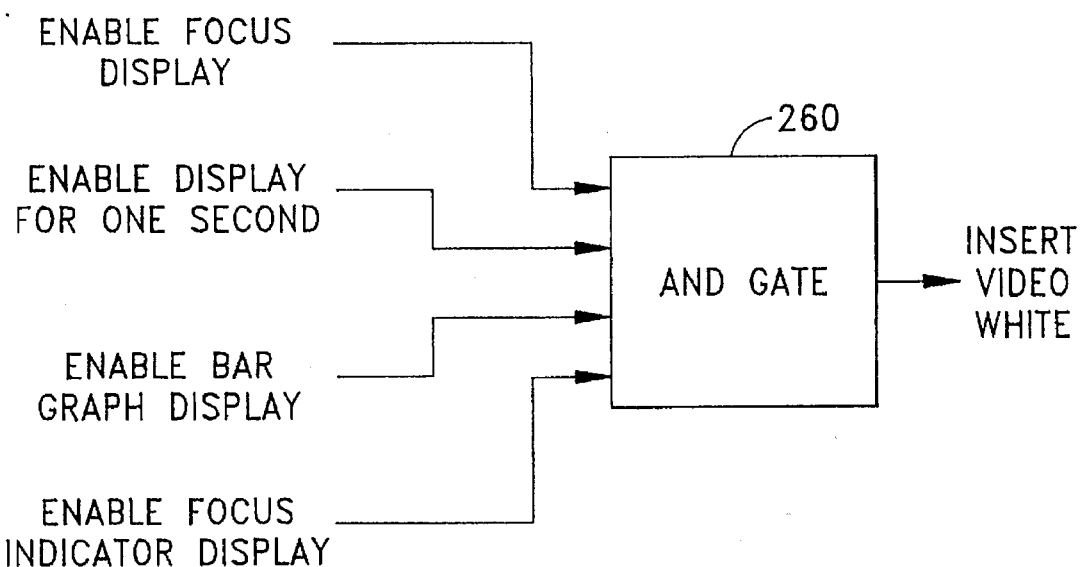
Figure 27B:
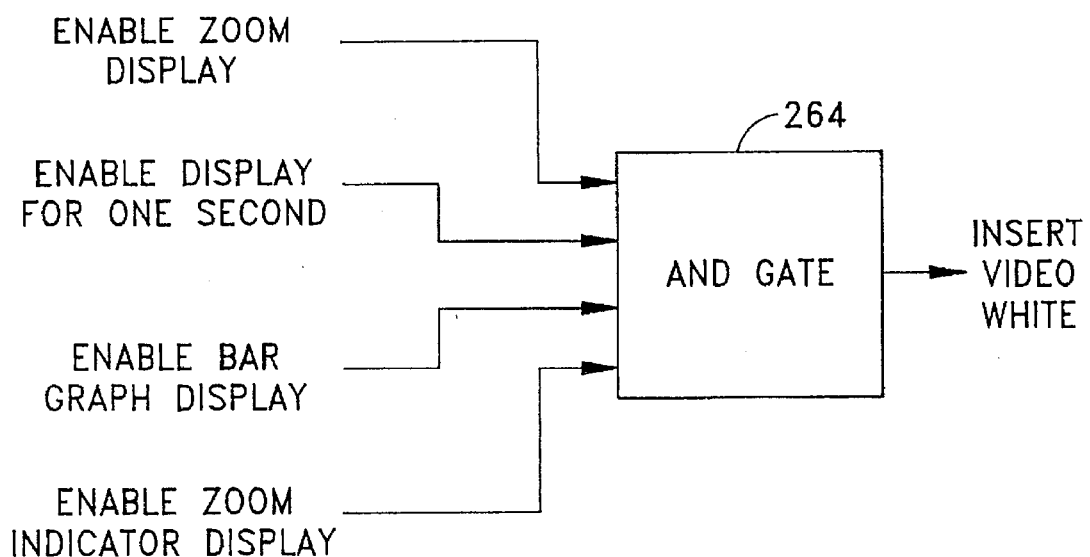

FIGS. 27A and 27B show AND gate circuits for causing the focus and zoom position markers to be generated. In FIG. 27A, AND gate 260 generates an "Insert Video White" signal for producing the focus position marker in response to the "Enable Focus Display", "The Enable Bar Graph Display" and the "Enable Focus Indicator Display" signal; also, in response to the "Enable Display For One Second" signal, it maintains that insert video white signal for an additional second after the focus control button that was depressed has been released. In FIG. 27B, the AND gate 264 generates an "Insert Video White" signal in response to the "Enable Zoom Display", "Enable Bar Graph Display" and the "Enable Zoom Indicator Display" signal and again, in response to the "Enable Display For One Second" signal, it also maintains that insert white signal for an additional second after the depressed zoom button has been released.

Figure 27C:
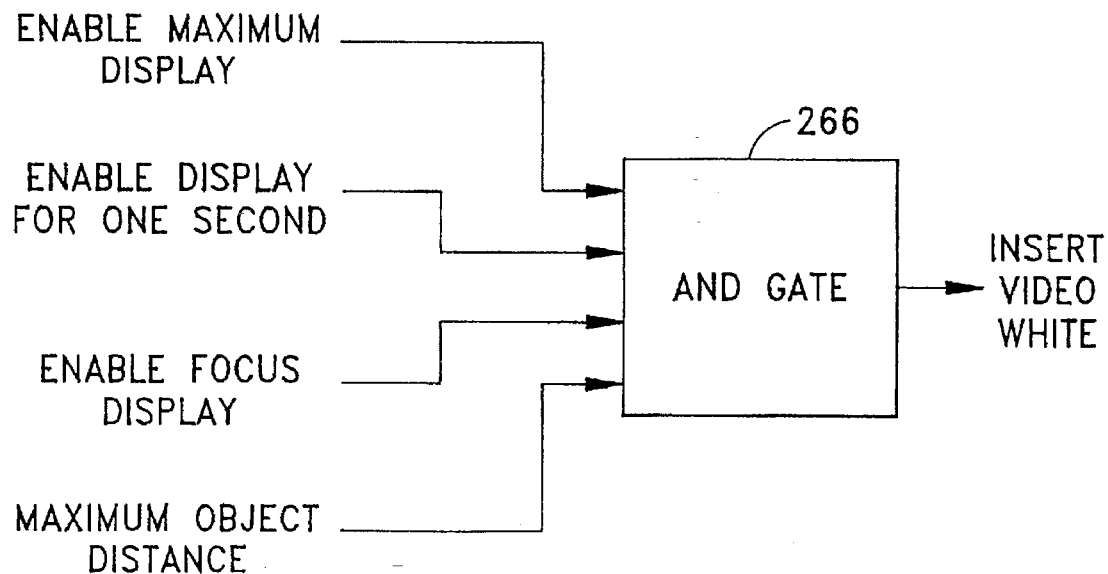
Figure 27D:
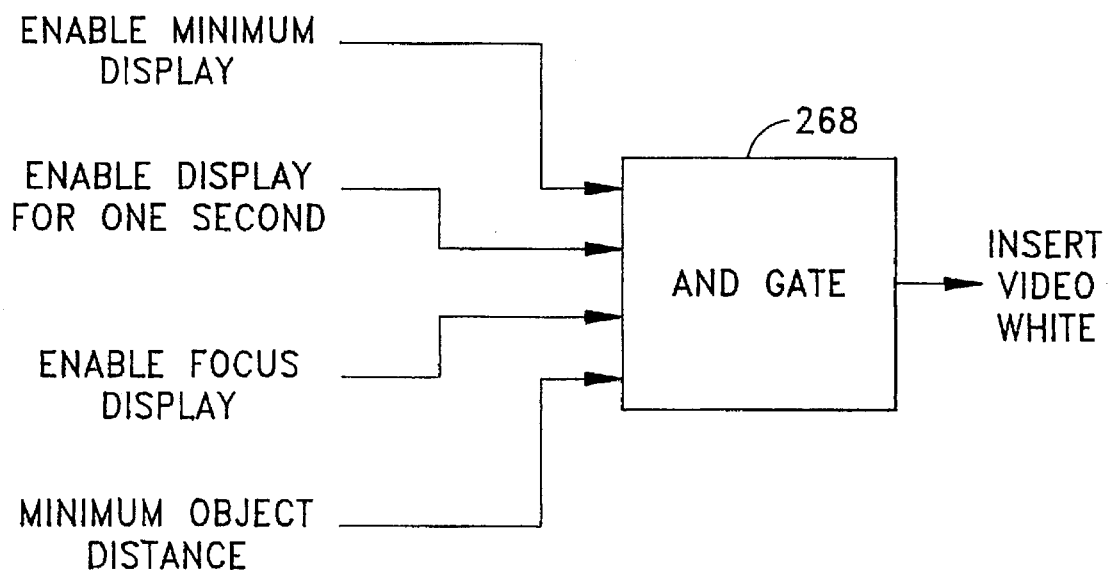

The two AND gate units of FIGS. 27C and 27D are similar to those of FIGS. 27A and 27B, except that with AND gate 266 the "Enable Maximum Display", "Enable Focus Display" and the "Maximum Object Distance" signals are used as inputs to the gate so as to cause the latter to produce an "Insert Video White" signal to generate a maximum focus limit marker, and with gate 268 the "Enable Minimum Display", "Enable Focus Display" and the "Minimum Object Distance" signals are used as inputs to the gate to generate an "Insert Video White" signal that produces the minimum focus limit marker. The "Enable Display For One Second" signal maintains the gate output for an additional second after the depressed focus button has been released.

Figure 27E:
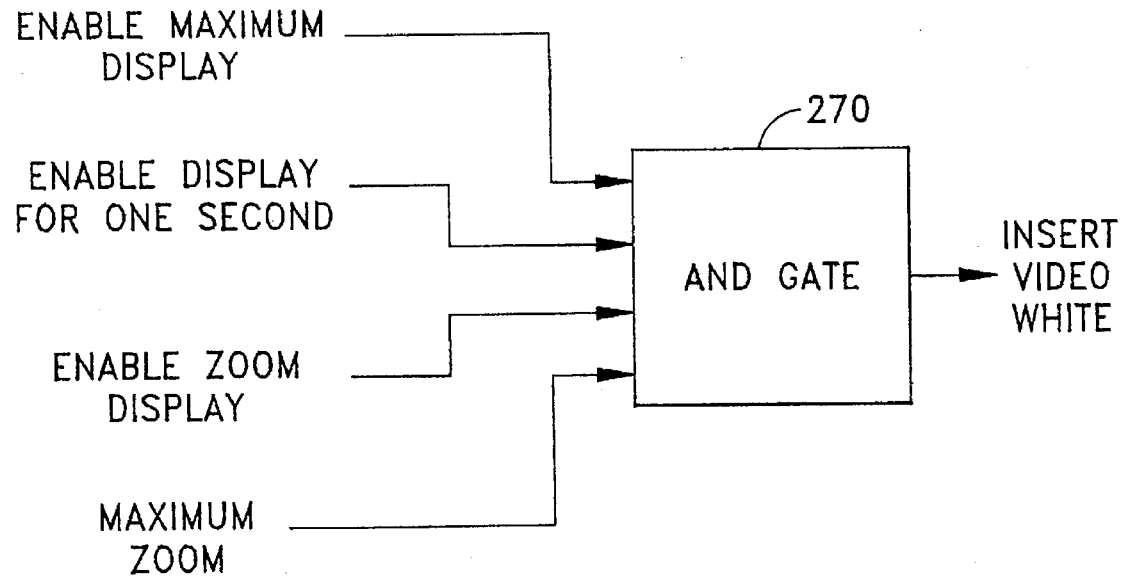
Figure 27F:
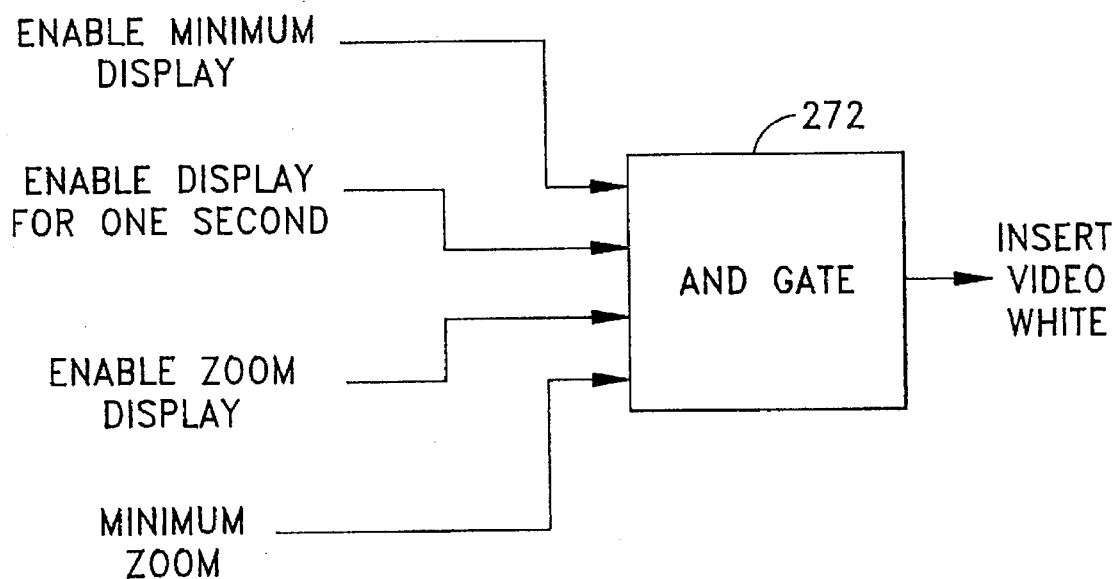

The AND gates 270 and 272 of FIGS. 27E and 27F are similar except that the "Enable Maximum Display", "Enable Zoom Display" and "Maximum Zoom" signals are used to cause gate 270 to produce an "Insert White Video" signal output to cause the monitor to display the minimum zoom limit marker. In FIG. 27F, the "Enable Minimum Display", "Enable Zoom Display" and "Minimum Zoom" signals are used to cause gate 272 to produce an "Insert White Video" signal output to cause the monitor to display the minimum zoom limit marker. The "Enable Display For One Second" signal maintains the output of gate 272 for an additional second after the depressed zoom button has been released.

Figure 28:
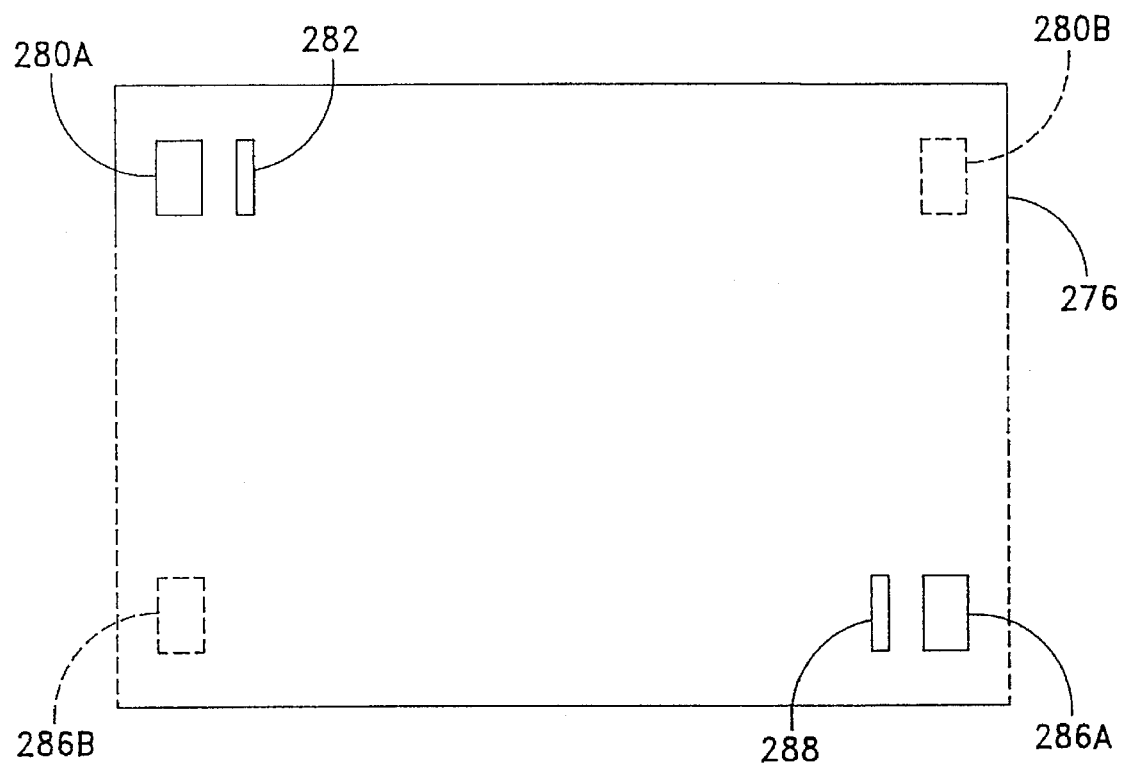
Figure 17:
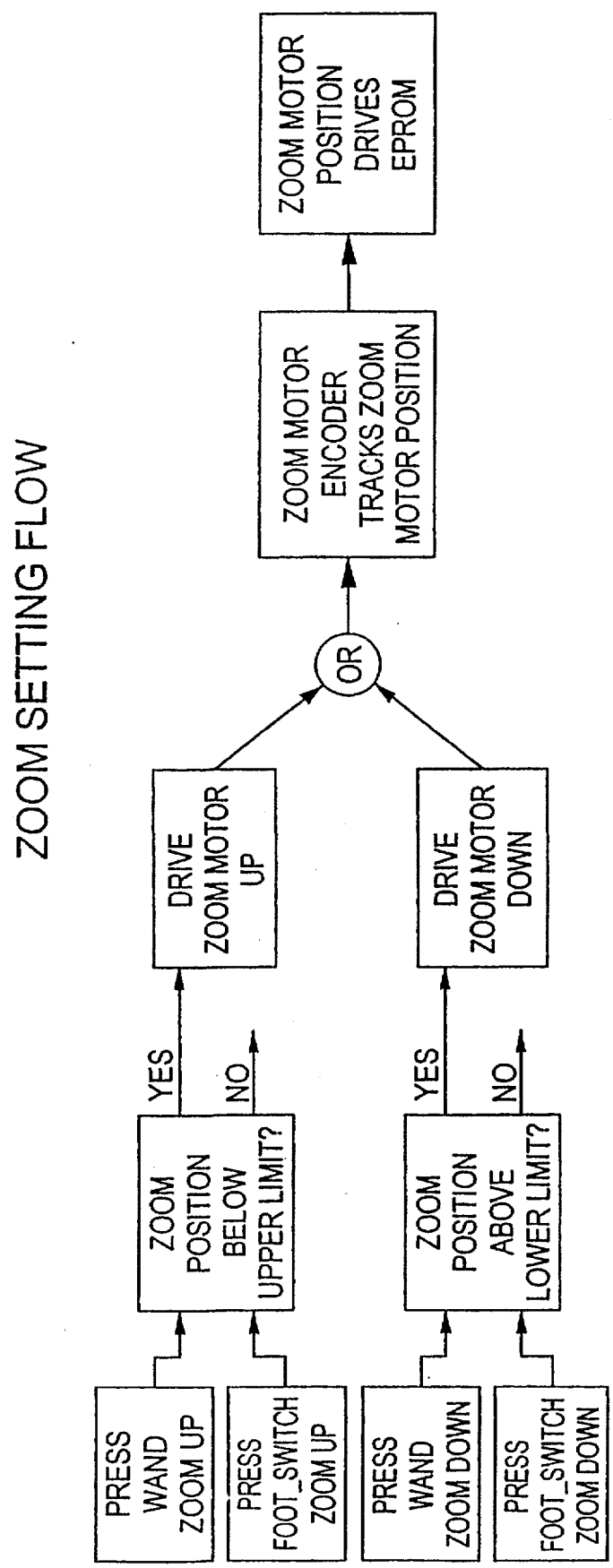

FIG. 28 illustrates the position and limit marker displays provided by this invention. The rectangle 276 represents the border of the endoscope image display on the TV monitor screen. For convenience of illustration, no endoscope image is presented in FIG. 28, but it is to be understood that the markers hereinafter described are superimposed on the displayed endoscope image.

The relatively large rectangle 280A represents the minimum end limit for the object distance (focus) parameter, while the smaller rectangle 282 represents the instantaneous bar-graph value of object distance parameter. The minimum focus limit marker 280A appears only when the object distance value represented by marker 282 approaches a predetermined minimum value. In practice, the circuits are set so that the instantaneous position markers and the limit markers never overlap. Instead it is preferred that each limit marker be generated so that it is spaced approximately ¼ inch from the corresponding instantaneous position marker when the latter has reached the limit of its travel. When the CCD imaging device is backed away from the object lens, the rectangle 282 moves to the right on the TV display to indicate a larger object distance value. As the rectangle 282 moves to the right, the larger end limit rectangular marker 280A will disappear. When the object distance value represented by rectangular marker 282 approaches its other (maximum) end limit, another large rectangle (shown in phantom at 280B) similar to rectangle 280A will appear at the right hand end of the image window 276.

The relatively large and relatively small rectangular markers 286A and 288 in FIG. 28 represent the maximum zoom position limit and the instantaneous zoom positions respectively. The marker 288 moves to the left as the zoom lens unit is moved forwardly in the endoscope. The larger end limit marker 286A appears only when marker 288 approaches the maximum end limit for the zoom lens unit, and disappears when marker 288 moves away from that markers end limit. Another minimum end limit marker 286B is displayed at the left hand side of the TV monitor screen when the instantaneous zoom position marker approaches the minimum (forward) end limit for the zoom lens unit.

The marker display capability provided by the present invention is advantageous to the operator in providing feedback as to the parameters of the zoom lens unit and the imaging device in relation to their maximum and minimum end limits.

The invention also offers the advantage that it is susceptible of various modifications. Thus, the shape of the markers is not limited to rectangles, and instead other shaped markers may be used. Also the marker display circuits can be modified so as to increase or decrease the length of time the markers are displayed and also to change the vertical positions of the markers on the TV monitor screen. Different forms of imaging devices also may be used. For example, the imaging component of the invention may utilize a BBD semiconductor imaging device rather than a CCD solid state element, as suggested by U.S. Pat. No. 4,488,039. Similarly, the number of lenses in the objective lens unit and also in the zoom lens unit may be changed without affecting operation of the invention.

Other possible modifications and advantages of the invention will be obvious to persons skilled in the art.

What is claimed is:

1. An endoscope apparatus comprising:

a handle assembly;

a tube having a distal end and a proximal end, said tube being mounted within said outer tube and having its proximal end anchored to said handle assembly;

an objective lens unit mounted in the distal end of said tube;

a shaft having a distal end and a proximal end, said shaft being disposed within and movable along the axis of said tube;

a solid state imaging device disposed within said tube and attached to said distal end of said shaft so as to be movable therewith along the axis of said tube, said imaging device having an light receiving surface for receiving an image transmitted by said objective lens unit and being capable of generating an output signal representative of the image transmitted by said objective lens unit;

a zoom lens unit disposed within said tube between said objective lens unit and said imaging device for transmitting images seen by said objective lens unit to said imaging device, said zoom lens unit being moveable along the axis of said tube relative to said objective lens unit so as to cause the magnification of the image passed by said objective lens unit to be changed in accordance with the axial position of said zoom lens unit in relation to said objective lens unit;

first and second drive means attached to said handle assembly;

a first motion-transmitting means coupling said first drive means to said shaft, whereby operation of said first drive means will cause axial movement of said imaging device relative to said objective lens unit;

a second motion-transmitting means coupling said second drive means to said zoom lens unit whereby operation of said second drive means will cause axial movement of said zoom lens unit relative to said objective lens unit and said zoom lens unit;

control means for operating said first and second drive means;

display means responsive to said imaging device output signal for generating a video reproduction of the image passed by said objective lens unit; and electronic means responsive to said imaging device output signal for causing said display means to generate a video image representative of the position of at least said zoom lens unit or said imaging device.

2. Apparatus according to claim 1 wherein said electronic means is adapted to cause said display means to generate a video image representative of the positions of both said zoom lens unit and said imaging device.

3. Apparatus according to claim 1 wherein said zoom lens unit is movable between a first minimum position and a second maximum position, and said electronic means is adapted to cause said display means to generate a first image representative of said minimum position of said zoom lens unit and a second image representative of said maximum position of said zoom lens unit.

4. Apparatus according to claim 3 wherein said electronic means is adapted to cause said display means to generate an additional image representative of the instantaneous position of said zoom lens unit.

5. Apparatus according to claim 1 wherein said imaging device is movable between a first minimum position and a second maximum position, and said electronic means is adapted to cause said display means to generate a first image representative of said minimum position of said imaging device and a second image representative of said maximum position of said imaging device.

6. Apparatus according to claim 5 wherein said electronic means is adapted to cause said display means to generate an additional image representative of the instantaneous position of said imaging device.

7. An endoscope apparatus comprising:

a handle assembly;

an outer tube having a distal end and proximal end, with said proximal end anchored to said handle assembly;

an inner tube having a distal end and a proximal end, said inner tube being mounted within said outer tube and having its proximal end anchored to said handle assembly;

an objective lens unit mounted in the distal end of said inner tube;

a shaft having a distal end and a proximal end, said shaft being disposed within and movable along the axis of said inner tube;

a solid state imaging device disposed within said inner tube and attached to said distal end of said shaft so as to be movable therewith along the axis of said inner tube, said imaging device having a light-receiving surface to receiving an image transmitted by said objective lens unit and being capable of generating an output signal representative of the image transmitted by said objective lens unit;

a zoom lens unit disposed within said inner tube between said objective lens unit and said imaging device, said zoom lens unit being moveable along the axis of said inner tube relative to said objective lens unit so as to cause the magnification of the image passed by said objective lens unit to be changed in accordance with the axial position of said zoom lens unit in relation to said objective lens unit;

first and second drive means attached to said handle assembly;

a first motion-transmitting means coupling said first drive lens to said shaft, whereby operation of said first drive means will cause axial movement of said imaging device relative to said objective lens unit;

a second motion-transmitting means coupling said second drive means to said zoom lens unit whereby operation of said second drive means will cause axial movement of said zoom lens unit relative to said objective lens unit and said zoom lens unit;

a space between said outer and inner tubes for transmitting light to illuminate an object viewed by said objective lens unit;

means attached to said handle assembly for connecting said proximal end of said light transmitting means to a light source;

control means for operating said first and second drive means;

display means responsive to said imaging device output signal for generating a video reproduction of the image passed by said objective lens unit; and means responsive to said imaging device output signal for causing said display means to generate a video image representative of the position of at least said zoom lens unit or said imaging device.

8. Apparatus according to claim 7 wherein said objective lens unit and said zoom lens unit have a common optical axis.

9. Apparatus according to claim 7 further including light-transmitting means disposed in said space between said inner and outer tubes, said light-transmitting means having a distal end and a proximal end with said distal end terminating at the distal end of said outer tube.

10. Apparatus according to claim 7 wherein said first and second drive means comprise first and second reversible electrical motors respectively.

11. Apparatus according to claim 10 further including user-operable switch means carried by said handle assembly for selectively operating said first and second electrical motors.

12. Apparatus according to claim 7 further comprising means for sensing the extent and direction of movement of said zoom lens unit and said imaging device relative to said objective lens unit and for producing output signals indicative of the extent and direction of said movement, and means for coupling said signals to said control means for use in controlling the relative positions of said zoom lens unit and said imaging device so that said imaging device is positioned at the focal plane of said zoom lens unit, whereby the image seen by said objective lens and projected by said zoom lens unit is in focus at the image-receiving surface of said imaging device.

13. Apparatus according to claim 7 further comprising first and second means for sensing the extent and direction of movement of said zoom lens unit and said imaging device respectively relative to said objective lens unit and for producing first and second output signals respectively indicative of the extent and direction of movement of said zoom lens unit and said imaging device respectively, and means for coupling said output signals to said control means for use in controlling the relative positions of said zoom lens unit and said imaging device so that at each position of said zoom lens unit said imaging device is positioned at the focal plane of said zoom lens unit, whereby the image seen by said objective lens and projected by said zoom lens unit is in focus at the image-receiving surface of said imaging device.

14. An endoscope apparatus comprising:

an inner tube having a distal end and a proximal end; an outer tube surrounding said inner tube;

a solid state imaging device mounted within and movable along said inner tube;

an objective lens unit mounted within and fixed to the distal end of said inner tube;

a zoom lens unit mounted within and movable along said inner tube; said zoom lens unit being disposed between said objective lens unit and said imaging device;

a plurality of light-transmitting fibers disposed between said inner and outer tubes, said fibers extending substantially to the distal end of said inner tube so that light transmitted thereby will illuminate the objective field;

first bi-directional electromechanical means for moving said zoom lens unit along said inner tube toward or away from said objective lens unit, said first electromechanical means comprising a first reversible electrical motor having an output shaft and first gear means coupling said output shaft to said zoom lens unit, whereby energization of said first motor will cause movement of said zoom lens unit along said inner tube according to the mode of energization of said motor; and second bidirectional electromechanical means for moving said imaging device along said inner tube toward or away from said objective lens unit and said zoom lens unit, said second electromechanical means comprising a second reversible electrical motor having an output shaft and second gear means coupling the output shaft of said second electrical motor to said imaging device, whereby energization of said second motor will cause movement of said imaging device along said inner tube according to the mode of energization of said second motor.

a solid state imaging device disposed within said tube and attached to said distal end of said shaft so as to be movable therewith along the axis of said tube, said imaging device having an light receiving surface for receiving an image transmitted by said objective lens unit and being capable of generating an output signal representative of the image transmitted by said objective lens unit;

display means responsive to said imaging device output signal for generating a video reproduction of the image passed by said objective lens unit; and means responsive to said imaging device output signal for causing said display means to generate a video image representative of the position of at least said zoom lens unit or said imaging device.

* * * * *

UNITED STATES PATENT AND TRADEMARK OFFICE
CERTIFICATE OF CORRECTION

PATENT NO.   : 5662584
DATED        : September 2, 1997
INVENTOR(S)  : Koichiro Hori et al.

It is certified that error appears in the above-indentified patent and that said Letters Patent is hereby corrected as shown below:

Claim 1, column 16, line 31, the word "an" should be -- a --;

Claim 7, column 17, line 42, the word "to" should be -- for --;

Claim 7, column 17, line 57, the word "lens" should be -- means --;

Claim 14, column 19, line 21, the period should be a semicolon; and

Claim 14, column 20, line 4, the word "an" should be -- a --.

Signed and Sealed this

Ninth Day of December, 1997

Attest:

BRUCE LEHMAN

*Attesting Officer*   Commissioner of Patents and Trademarks

UNITED STATES PATENT AND TRADEMARK OFFICE
CERTIFICATE OF CORRECTION

PATENT NO. : 5,662,584
DATED : September 2, 1997
INVENTOR(S) : Koichiro Hori et al.

It is certified that error appears in the above-identified patent and that said Letters Patent is hereby corrected as shown below:

IN THE DRAWINGS:

In Fig. 17, the box labeled "DRIVE FOCUS MOTOR UP" should be changed to read -- DRIVE ZOOM MOTOR UP --; and In Fig. 17, the box labeled "DRIVE FOCUS MOTOR DOWN" should be changed to read -- DRIVE ZOOM MOTOR DOWN ,-- as shown on the attached page.

Signed and Sealed this

First Day of December, 1998

Attest:

BRUCE LEHMAN

Attesting Officer

Commissioner of Patents and Trademarks